United States Patent
Cannon et al.

(10) Patent No.: US 9,792,660 B2
(45) Date of Patent: Oct. 17, 2017

(54) CLINICIAN TO DEVICE ASSOCIATION

(75) Inventors: Paul Cannon, Kansas City, MO (US);
Damon Matthew Herbst, Shawnee, KS (US); Mark Allen Nolte, Lee's Summit, MO (US)

(73) Assignee: Cerner Innovation, Inc., Kansas City, KS (US)

(*) Notice: Subject to any disclaimer, the term of this patent is extended or adjusted under 35 U.S.C. 154(b) by 69 days.

(21) Appl. No.: 12/567,956

(22) Filed: Sep. 28, 2009

(65) Prior Publication Data

US 2010/0287006 A1 Nov. 11, 2010

Related U.S. Application Data

(63) Continuation-in-part of application No. 12/347,475, filed on May 7, 2009.

(51) Int. Cl.
 *G06Q 50/22* (2012.01)
 *G06Q 50/24* (2012.01)
 *G06F 19/00* (2011.01)
 *G06Q 10/06* (2012.01)

(52) U.S. Cl.
 CPC .......... *G06Q 50/22* (2013.01); *G06F 19/327* (2013.01); *G06F 19/3406* (2013.01); *G06Q 10/06* (2013.01); *G06Q 50/24* (2013.01)

(58) Field of Classification Search
 CPC ........ G06Q 50/22; G06Q 50/24; G06Q 10/10; G06Q 50/00; G06Q 10/06; G06Q 10/103
 USPC .......................................... 705/2, 3
 See application file for complete search history.

(56) References Cited

U.S. PATENT DOCUMENTS

| | | | |
|---|---|---|---|
| 7,444,291 B1 | 10/2008 | Prasad et al. | |
| 7,716,072 B1 | 5/2010 | Green, Jr. et al. | |
| 2002/0013516 A1 | 1/2002 | Freyre et al. | |
| 2003/0140928 A1* | 7/2003 | Bui et al. | 128/898 |
| 2004/0176667 A1* | 9/2004 | Mihai et al. | 600/300 |
| 2005/0075904 A1 | 4/2005 | Wager et al. | |
| 2006/0047538 A1 | 3/2006 | Condurso et al. | |
| 2006/0069717 A1 | 3/2006 | Mamou | |
| 2008/0015903 A1 | 1/2008 | Rodgers | |
| 2008/0046292 A1 | 2/2008 | Myers et al. | |
| 2008/0077447 A1 | 3/2008 | Jung et al. | |
| 2008/0126126 A1* | 5/2008 | Ballai | 705/2 |
| 2009/0099866 A1* | 4/2009 | Newman | G06F 19/327 705/2 |

(Continued)

OTHER PUBLICATIONS

Non-Final Office Action mailed Dec. 9, 2010 re U.S. Appl. No. 12/347,475, filed Dec. 31, 2008, 19 pages.

(Continued)

*Primary Examiner* — Maroun Kanaan
(74) *Attorney, Agent, or Firm* — Shook, Hardy & Bacon L.L.P.

(57) ABSTRACT

Embodiments of the invention are directed to methods of providing data feeds from medical devices associated with patients to computing devices associated with clinicians. A computing device for each of a number of clinicians is registered as being associated with the clinician. An identification of a patient is received. A list of medical devices related to the patient is retrieved. An identification of a number of clinicians is received. The medical devices are associated with the computing devices of the clinicians. Data feeds are provided to the computing devices from the medical devices.

20 Claims, 27 Drawing Sheets

(56) References Cited

U.S. PATENT DOCUMENTS

| | | |
|---|---|---|
| 2009/0119124 A1 | 5/2009 | Kambaloor |
| 2009/0182594 A1 | 7/2009 | Choubey |
| 2009/0204434 A1 | 8/2009 | Breazeale, Jr. |
| 2010/0010859 A1 | 1/2010 | Ratakonda et al. |
| 2011/0001605 A1 | 1/2011 | Kiani et al. |
| 2011/0054936 A1 | 3/2011 | Cowan et al. |
| 2013/0096936 A1 | 4/2013 | Sampath et al. |

OTHER PUBLICATIONS

Final Office Action mailed Aug. 5, 2011 re U.S. Appl. No. 12/347,475, filed Dec. 31, 2008, 23 pages.
Non-Final Office Action mailed Dec. 23, 2010 re U.S. Appl. No. 12/347,487, filed Dec. 31, 2008, 15 pages.
Final Office Action mailed Jul. 13, 2011 re U.S. Appl. No. 12/347,487, filed Dec. 31, 2008, 20 pages.
Non Final Office Action of U.S. Appl. No. 12/567,174, mailed Jan. 19, 2012, 13 pages.
Final Office Action in U.S. Appl. No. 12/567,174, mailed Jul. 31, 2012, 12 pages.
Non Final Office Action in U.S. Appl. No. 12/567,174, mailed Sep. 11, 2013, 22 pages.
PreInterview First Action Interview in U.S. Appl. No. 13/236,339, mailed Oct. 22, 2013, 14 pages.
PreInterview First Action Interview in U.S. Appl. No. 13/236,343, mailed Oct. 22, 2013, 14 pages.
Non-Final Office Action dated Sep. 22, 2014 in U.S. Appl. No. 13/236,343, 11 pages.
Non-Final Office Action dated Sep. 23, 2014 in U.S. Appl. No. 13/236,339, 9 pages.
Non-Final Office Action dated Jun. 19, 2014 in U.S. Appl. No. 12/347,487, 14 pages.
Non-Final Office Action dated Jul. 7, 2014 in U.S. Appl. No. 12/567,174, 11 pages.
Non-Final Office Action dated Jul. 18, 2014 in U.S. Appl. No. 12/347,475, 13 pages.
Non-Final Office Action dated Mar. 13, 2015 in U.S. Appl. No. 12/347,487, 16 pages.
Final Office Action dated Mar. 17, 2015 in U.S. Appl. No. 12/347,475, 16 pages.
Final Office Action dated Mar. 27, 2015 in U.S. Appl. No. 12/567,174, 11 pages.
Final Office Action dated Jun. 11, 2015 in U.S. Appl. No. 13/236,343, 5 pages.
Final Office Action dated Jun. 11, 2015 in U.S. Appl. No. 13/236,339, 5 pages.
Non-Final Office Action dated Dec. 30, 2015 in U.S. Appl. No. 12/347,487, 16 pages.
Non-Final Office Action dated Jan. 7, 2016 in U.S. Appl. No. 12/567,174, 14 pages.
Non-Final Office Action dated Feb. 12, 2016 in U.S. Appl. No. 13/236,343, 6 pages.
Non-Final Office Action dated Mar. 1, 2016 in U.S. Appl. No. 13/236,339, 6 pages.
Final Office Action dated May 31, 2016 in U.S. Appl. No. 13/236,343, 7 pages.
Final Office Action dated Jul. 15, 2016 in U.S. Appl. No. 12/347,487, 23 pages.

\* cited by examiner

1600

```
┌─ ☐ ORDER ASSOCIATION ─────────────────────── _ ▢ ✕ ┐
│ ┌──────────────────────────────────────────────┐ │
│ │ SMITH, JOSEPH      MALE          SICU        │ │ ← 1610
│ │ 01/01/2000         8 YEARS                   │ │
│ ├──────────────────────────────────────────────┤ │ ← 1612
│ │ DEVICE 2 <STATUS>                            │ │
│ │ PATIENT ⊘ | DEVICE ⊘ | ORDER ⊘ | ROUTE ✖ | TIME ✖ │ │
│ ├──────────────────────────────────────────────┤ │ ← 1614
│ │ CONNECTED DEVICES                            │ │
│ │                                              │ │
│ │                                              │ │
│ ├──────────────────────────────────────────────┤ │ ← 1616
│ │ SUGGESTED ORDERS                             │ │
│ │                                        ⌃ ⌄   │ │
│ │ ☐ DEXTROSE 5% WITH 0.3% NACL 1000ML + POTASSIUM CHLORIDE 4...─⌃ │ │ ← 1620
│ │   RATE: <>                                   │ │
│ │   VOLUME TO INFUSE: <>                       │ │ ← 1618
│ │   DOSE: <>                                   │ │
│ │   ☑ DEXTROSE 5% WITH 0.3% NACL 1000ML        │ │
│ │   ☐ POTASSIUM CHLORIDE 40MEQ                 │ │
│ │ ☐ DEXTROSE 5% WITH 0.3% NACL 1000 ML ──────⌃ │ │ ← 1624
│ │   RATE: <>                                   │ │
│ │   VOLUME TO INFUSE: <>                       │ │ ← 1622
│ │   DOSE: <>                                   │ │
│ │ ☐ DEXTROSE 5% WITH 0.3% NACL 1000 ML ──────⌃ │ │ ← 1628
│ │   RATE: <>                                   │ │
│ │   VOLUME TO INFUSE: <>                       │ │ ← 1626
│ │   DOSE: <>                                ⌄  │ │
│ │                                              │ │
│ │        ( DISASSOCIATE ) ( ASSOCIATE ) ( CLOSE ) │ │
│ └──────────────────────────────────────────────┘ │
└──────────────────────────────────────────────────┘
```

*FIG. 16.*

CLINICIAN TO DEVICE ASSOCIATION

CROSS-REFERENCE TO RELATED APPLICATIONS

This application is a continuation-in-part application of U.S. patent application Ser. No. 12/347,475 entitled "Patient to Device Association" filed on Dec. 31, 2008 and is related by subject matter to U.S. patent application Ser. No. 12/347,487 entitled "Patient to Device Association Based on Suggested Devices" filed on Dec. 31, 2008, the entirety of both applications are incorporated in this application by reference.

BACKGROUND

Typically, medical devices that are used to treat or care for a patient are not adequately linked to that patient in the patient's record, such as an electronic medical record (EMR). In many instances, this lack of linkage or association may lead to many inaccuracies and inconsistencies in treating the patient. For instance, when a caregiver, such as a nurse, begins an ordered dosage using an infusion pump, the nurse may write down or enter a start time of the infusion in the patient's record. An inaccuracy may arise when the start time is determined based on a watch or clock that is not accurate, or in sync with the watch or clock used to document the end time. Further, the lack of association between a patient and medical devices used to treat the patient may necessitate multiple queries in order to locate certain information related to the patient's treatment. For instance, even if a particular patient's record is queried and found, data from the medical devices used in conjunction with the patient's treatment may not be included in the record, but may require separate and multiple queries. In some cases, the data from the medical devices may be very difficult, or even impossible to locate. Additionally, lack of association between various clinicians and the medical devices used to treat the patient may necessitate each clinician to perform multiple queries, both to locate appropriate devices and to receive various data feeds from the medical devices once they have been located.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention are directed to methods of providing data feeds from medical devices associated with patients to computing devices associated with clinicians. A computing device for each of a number of clinicians is registered as being associated with the clinician. An identification of a patient is received. A list of medical devices related to the patient is retrieved. An identification of a number of clinicians is received. The medical devices are associated with the computing devices of the clinicians. Data feeds are provided to the computing devices from the medical devices.

BRIEF DESCRIPTION OF THE DRAWINGS

Embodiments are described in detail below with reference to the attached drawing figures, wherein:

FIG. 16 is an illustrative screen display showing a selected patient, a selected medical device, and a plurality of orders, in accordance with an embodiment of the present invention;

DETAILED DESCRIPTION

Figure 1:
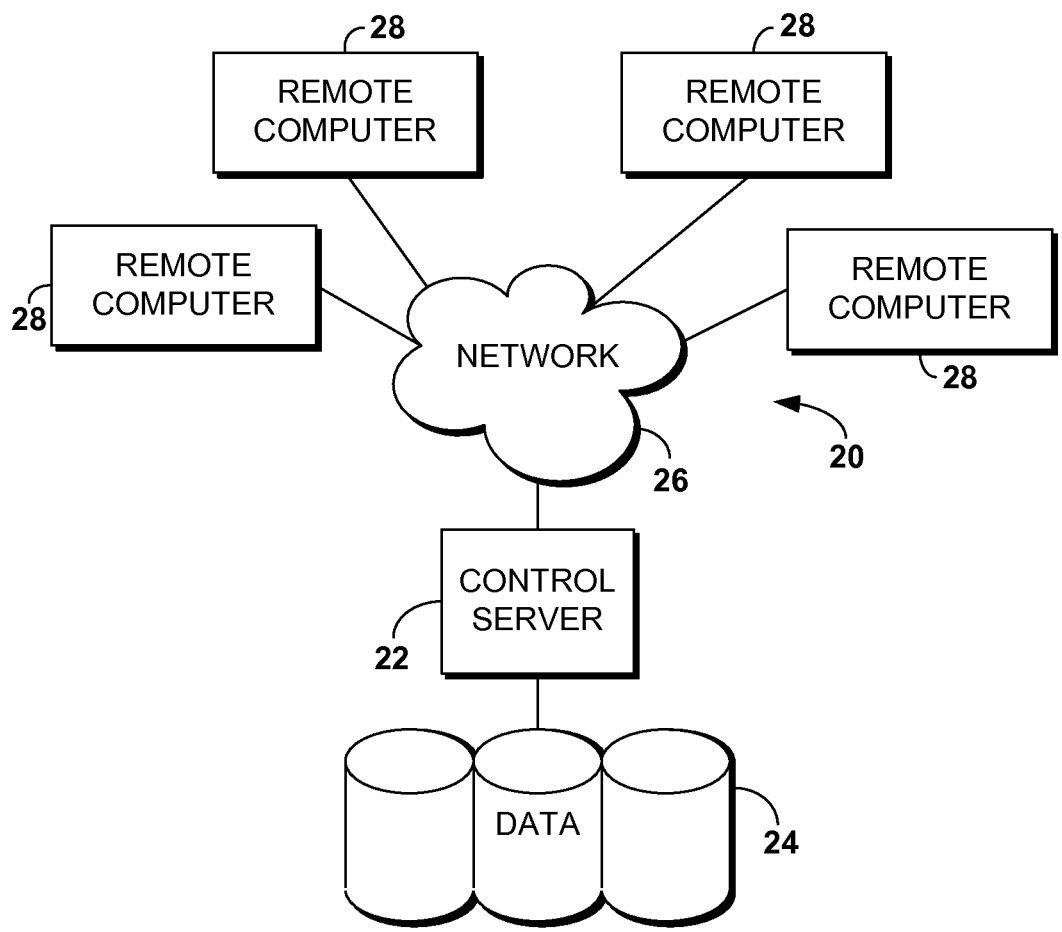
FIG. 1 is a block diagram of an exemplary computing environment suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide systems, methods, and computer-readable media for, among other things, associating a patient and a medical device to one another, and for associating a medical device and an order to one another. Initially, a medical device may be any device, stationary or otherwise, that may be used to treat a patient in a hospital, doctor's office, etc. For exemplary purposes only and not limitation, medical devices may include monitors, ventilators, pumps (e.g., infusion pumps, balloon pumps), a patient's bed, sequential compression devices, electronic security devices, and the like. Some medical devices may be capable of being associated with orders, and others may not, such as a patient's bed, monitors, ventilators, etc. Orders are typically given or made by clinicians who are authorized to give such orders, and may vary depending on the patient, or by type of device required, if any, to carry out a particular order.

Once a patient and device have been associated, data from that device may be continuously received until the patient and device are disassociated. For instance, a clinician or other user may choose to disassociate an existing association. This may be done in many ways, including scanning or otherwise identifying the patient and device, and selecting a disassociate button located on the screen display. In embodiments, checkboxes are displayed near each device identification to allow for a user to quickly select and disassociate a particular device from the patient who is identified on that screen display. In another instance, an indication that the first medical device is offline, or is no longer connected to the bus, for example, may be received, which also may disassociate the device from the patient. Additionally, in yet another instance, an override caused by the association of another patient to a device may automatically cause a disassociation event to occur. When an indication is received to associate a patient with a medical device that is already associated to another patient, an alert may be provided to a user by way of a dialog box or other alert mechanism, which may allow the user to choose whether an override of the existing association should occur.

In embodiments of the present invention, medical devices and orders may be suggested based on one of many factors. In one instance, medical devices may be suggested based on various demographics of the identified patient, including, but not limited to, the patient's age, weight, or gender. Alternatively, medical devices may be suggested based on the patient's location in the hospital or medical building. For instance, if a patient is admitted to a hospital and will be located in an intensive care unit (ICU), devices that are typically used in an ICU or devices currently located in the ICU may be suggested as devices with which that patient may need to be associated. In another instance, medical devices may be suggested based upon an identified order. As will be discussed in greater detail below, certain orders correspond with certain devices, as they require certain devices to be carried out. Additionally, orders may be suggested based upon an identified patient, as orders are typically made for a particular patient.

In various embodiments of the present invention, data from various medical devices may be transferred or routed to a patient's electronic medical record (EMR). As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare.

In other embodiments of the invention, a number of clinicians could be associated with a patient. A number of medical devices associated with the patient could be associated with computing devices associated with each of the clinicians. There are a number of devices suitable for use as a computing device by a clinician. By way of example, mobile phones and digital assistants could be used as computing devices. Laptops are another example of a suitable computing device. Clinicians could include a number of clinical personnel. For example, doctors and nurses could be clinicians.

Data feeds from the associated medical devices could be transmitted to the digital computing devices. The data feeds could be continuous data feeds from various medical devices. The data feeds could also include various alerts. Additionally, the data feeds could be divided into tiers, where each tier could be sent to various clinicians, depending on the type of clinician. For example, nurses could get data feeds from some tiers while doctors receive data feeds from other tiers. Tiers could be used for subscription purposes as well. By way of example, a doctor could subscribe to all data feeds in a particular tier from all the medical devices associated with a particular patient.

An embodiment of the invention is directed to a method of providing data feeds from medical devices associated with patients to computing devices associated with clinicians. A computing device for each of a number of clinicians is registered as being associated with the clinician. An identification of a patient is received. A list of medical devices related to the patient is retrieved. An identification of a number of clinicians is received. The medical devices are associated with the computing devices of the clinicians. Data feeds are provided to the computing devices from the medical devices.

Another embodiment is directed to a method of providing data feeds from medical devices associated with patients to computing devices associated with a clinician. An identification of a patient is received. A list of medical devices associated with the patient is retrieved. An indication of a clinician and an associated computing device is received. The medical devices are associated with the computing device. Data feeds from the medical devices are provided to the computing device.

A further embodiment of the invention is direct to a method of providing data feeds from medical devices to computing devices associated with clinicians. A computing device is registered as an associated computing device to each of a number of clinicians. An identification of a patient is received from one or more clinicians. A list of medical devices associated with the patient is retrieved. An indication of one or more clinicians is received. The medical devices are associated with the computing devices of the identified clinicians. A continuous data feed from each of the medical devices is provided to each computing device of each of the clinicians. The continuous data feeds include at least one continuous feed of alerts from one or more of the medical devices.

Having briefly described embodiments of the present invention, an exemplary operating environment suitable for use in implementing embodiments of the present invention is described below.

Referring to the drawings in general, and initially to FIG. 1 in particular, an exemplary computing system environment, for instance, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2:
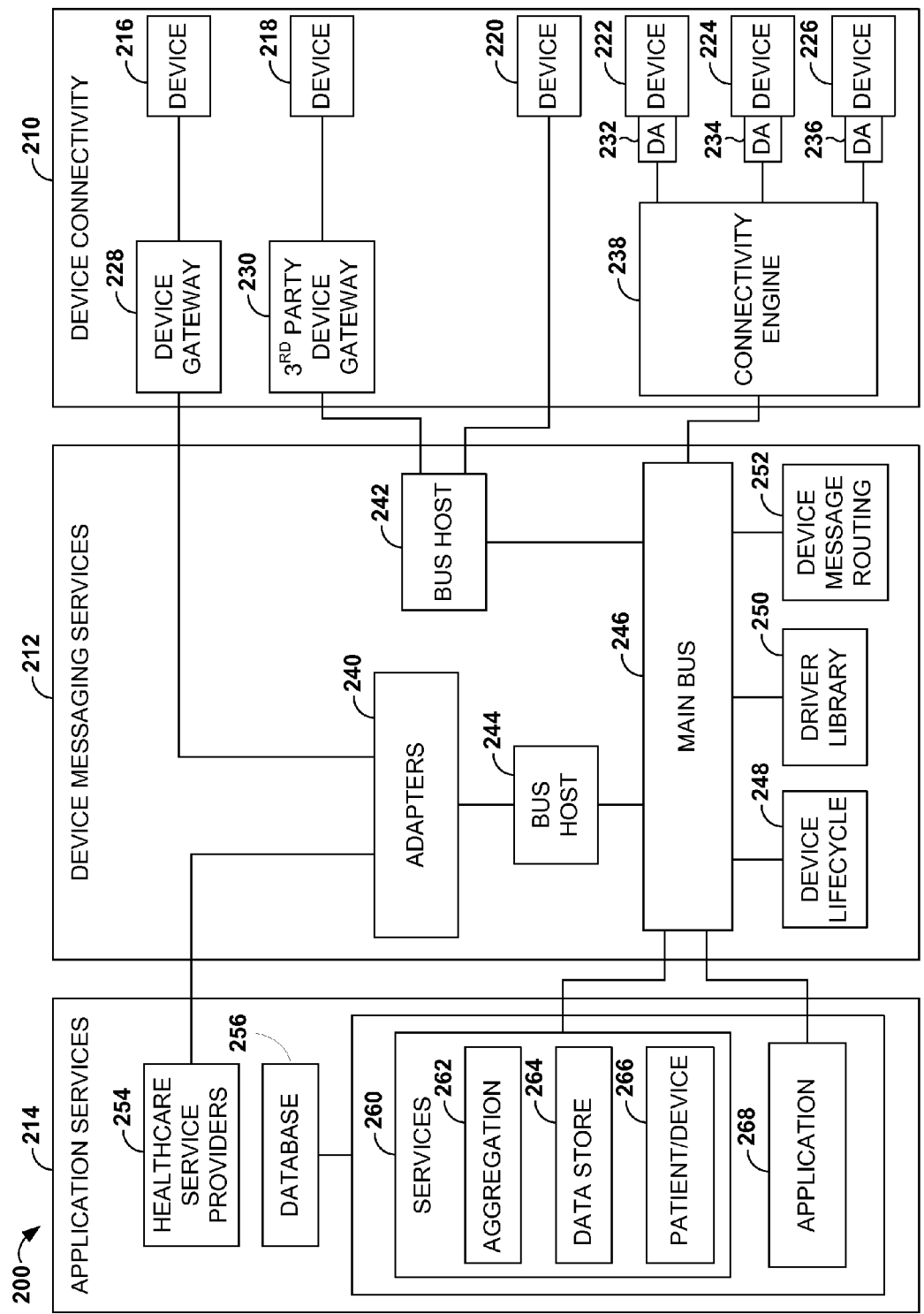
FIG. 2 is an exemplary system architecture suitable for use in implementing embodiments of the present invention.

FIG. 2 is an exemplary system architecture 200 suitable for use in implementing embodiments of the present invention. Generally, the exemplary system architecture 200 advantageously allows for communication with medical devices, for example, through a bus or server, instead of communication directly with the medical devices. A patient to device association may be initiated, and the existence of a bus or server may assist in maintaining that association until the occurrence of a disassociation event. If a computing device, such as a PDA, for example, were to communicate directly with a medical device, the relationship or association between the patient and medical device may terminate when that particular medical device is no longer being used for that particular patient. There may be instances, however, when a caregiver may want the association between that patient and medical device to continue until the occurrence of some disassociation event. In that case, a bus may assist in maintaining and managing that relationship.

Initially, the exemplary system architecture 200 includes device connectivity 210, device messaging services 212, and application services 214. The device connectivity 210 includes one or more medical devices that are connected to the device messaging services 212 such that the devices may, at a later time, be associated to a particular patient and/or an order. These devices may include, but are not limited to monitors, cardiac ventilators, balloon pumps, patient beds, infusion pumps, sequential compression devices, electronic security devices, vital signs devices, or any other device that a health care provider may use for a patient while the patient is in the hospital. These devices are shown in FIG. 2 as items 216, 218, 220, 222, 224, and 226.

Each medical device may communicate with the device messaging services 212 in a different way. For example, some devices, such as device 216, may utilize a device gateway 228. A gateway is generally a device that connects networks or other devices using different communications protocols so that information can be easily passed from one to the other. A gateway may both transfer information and convert it to a form compatible with the protocols used by the receiving network. Here, the device gateway assists in the transfer of data from the device 216 to the device messaging services 212. As will be described in greater detail below, an adapter, such as adapter 240 may be used in instances where the device gateway 228, was provided by the device manufacturer. The adapter 240 is typically used to facilitate communication from a consumer to the gateway over the consumer's protocol. It should be noted that an adapter may reside on or near the device messaging services, or may reside near the actual device or device gateway. In other instances, a device gateway may be a third-party device gateway 230. In these instances, an adapter may not be necessary, as the device messaging services 212 may already know what type of messages to expect from that device 218 through the third-party device gateway 230. Many different connection types may be utilized between devices, gateway servers, and components of the device messaging services 212, including, but not limited to, HL7 TCP/IP, a software development kit (SDK), RS 232, etc.

Other devices, such as device 220, may have an internal gateway or other component such that a gateway like 228 or 230 would not be needed. These devices may have all of the required capability built into it, and, if necessary, may even have their own adapters incorporated therein such that a separate adapter would not be necessary. Still other devices, such as devices 222, 224, and 226, may be legacy devices that are older and don't have networking built-ins. For example, it may not be possible to plug in a CAT 5 network to the legacy devices, the devices may not have wireless networking capabilities, etc. A serial port may be the only connection mechanism that exists on these devices. For these devices, a connectivity engine 238 and device adapters 232, 234, and 236 may be used. The device adapter is a hardware device that is affixed directly onto the medical device, and acts as the sole source of identification and connection to the connectivity engine 238. Device adapters 232, 234, and 236 are configurable with device specific information including, but not limited to, manufacturer, device name, device model, port settings, and the like. Device adapters 232, 234, and 236 may use various connection mechanisms to connect to the connectivity engine 238 including, but not limited to, Universal Serial Bus (USB) or Personal Area Network (PAN). The connectivity engine 238 is a piece of hardware that may be connected to devices 222, 224, and 226 either wirelessly or via a wired connection. Even if there is a wired connection between the connectivity engine 238 and a device, there may still be a wireless connection over a wireless network between the connectivity engine 238 and the device messaging services 212.

The connectivity engine 238 may also assist in detecting types of devices so that the appropriate driver may be loaded, which may be based on the make and model of the particular device. The connectivity engine 238 may be located on the device messaging services 212 or as part of the device subsystems 210, as illustrated in FIG. 2. The device messaging services 212 or a component thereof may communicate with the connectivity engine 238 to establish a connection to the device itself. In one embodiment, the connectivity engine 238 may be physically present in a patient's room so that when a new device, such as a legacy device, is brought into that room, it may be connected to the connectivity engine 238 if needed. At that time, a connect event may occur, and the device messaging services 212 may broadcast the connect event to other components who may need to know.

The medical devices, either directly or indirectly through a gateway, connectivity engine, or other component are connected to the device messaging services 212. The device messaging services 212, in some embodiments, may generally include one or more adapters 240, one or more bus hosts, such as bus hosts 242 and 244, a main bus 246, a device lifecycle 248, a driver library 250, and a device message routing 252. As previously described, an adapter may be used when the device gateway, such as device gateway 228, is provided by the manufacturer of a device, for example. The adapter 240 assists to facilitate communication from a consumer to the gateway over the consumer's protocol. While one adapter 240 is illustrated in FIG. 2, it is contemplated to be within the scope of the present invention that more than one adapter 240 may be used. In one embodiment, one adapter 240 may be used for more than one medical device, but in another embodiment, each medical device requiring an adapter may require a separate adapter. Further, the adapter 240 may be used to communicate data from the device messaging services 212 to healthcare providers 254. In these cases, the data may not be transferred through any services or applications, but may be transferred directly to other healthcare providers 254.

A bus host, such as bus host 242 or 244 may be used to perform several functions, including, but not limited to, detecting hardware that is plugged in or directly connected to the host, loading appropriate device drivers after the device has been identified, dynamically locating and installing drivers if the driver is not currently present on the host, and for unloading the device driver after the device has been disconnected. A bus host may not be utilized for each and every medical device, but may be used for some that don't have device adapters, for example, which perform many of the functions listed above. The embodiment of FIG. 2, for example, has a bus host for devices 216, 218, and 220, which are not shown as having device adapters, such as device adapters 232, 234, and 236, nor do they require use of the connectivity engine 238. In addition to the above described functionality of the bus hosts 242 and 244, they may also allow for communication to the device to get various types of information to and from the device. This information may be, for example, determining whether the bed rails are up or down, or even determining the patient's weight when the patient is sitting or lying on the bed.

The main bus 246 provides connection framework, as it may create and manage all connections to the device messaging services 212. The main bus 246 also provides messaging architecture for the device messaging services 212. The main functionality of the main bus 246 includes providing general operational and management capabilities for connected devices, which may vary depending on the service that is subscribing or requesting the data from the devices.

A device lifecycle 248 may detect the presence of a device on the main bus 246. The device lifecycle 248 also may maintain an accurate directory of currently connected medical devices to the main bus 246 as various medical devices become connected. Further, it may ensure "active" connectivity of a medical device to the main bus 246 via a device heartbeat. A heartbeat is an indication given at a certain interval of time that a particular medical device is connected to the main bus 246. This interval may vary, and may be regular, such as every 20 seconds, for example. Additionally, the interval may depend on each medical device. As a medical device deregisters, or becomes unconnected to the main bus 246, the device lifecycle 248 may be responsible for sending out a notice of a disconnect event, and will then stop sending that device's heartbeat out to certain components that require that information. There are various phases of the device lifecycle 248, which may include, in one embodiment, a notification phase that notifies of an event generated at the device connection and of a device connected as directly to the main bus 246; an interrogation phase; an identification phase that identifies the vendor, make, model, etc. of each medical device and that finds and downloads the appropriate driver when necessary; an activation phase that loads the device driver and registers the medical devices; and an execution phase that is responsible for tracking the medical devices' heartbeats and gathers and transmits data to and from the medical devices.

A driver library 250 may store a plurality of drivers that may be used and installed on particular devices, when required. Further, a device message routing component 252 handles routing messages from source to destination across the device messaging services 212. Messages may take on a variety of forms, and may contain vastly different types of content. Various types of messaging may include request and reply messaging, publish and subscribe messaging, and asynchronous one-way messaging. Request and reply messaging includes taking a message from a source, routing it to a single destination, and routing a reply message from the destination back to the original source. Publish and subscribe messaging involves a publisher sending messages out on a named topic, which may be received by multiple subscribers. Asynchronous one-way messaging includes doing requests and reply messaging without needing to receive a reply. The only receipt message may be an indication that the message was successfully sent.

With continued reference to FIG. 2, application services 214 includes various components, including healthcare providers 254, a database 256, services 260, and an application 268. The services 260 may consume some or all of the information that the main bus 246 provides. In some instances, the services 260 may be application programming interfaces (APIs), which may support requests made by computer programs, such as applications. For instance, the services 260 may use the main bus 246 to determine where a connected device is located. The services 214 may include various components that may all utilize information sent by the main bus 246. These may include, for example, an aggregation component 262, a data store 264, and a patient to device association 266, which is further discussed herein. The aggregation component 262 allows for a user to query a patient by a patient identification over a large number of patient identifications. Once a match is found, information relating to that patient, such as devices that the patient is associated with, may be retrieved. The data store 264 stores data that is published by the medical devices.

In various embodiments of the present invention, the services 260 run on the main bus 246, and thus together with the main bus 246, may provide additional functionality to the system as a whole. For example, when various services 260 run on the main bus 246, the main bus 246 may store discrete data posts, such as heart rate, systolic blood pressure, diastolic blood pressure, etc., in a data store, such as data store 264, for historical queries and archiving. Further, the main bus 246 may chart acquired discrete data into a patient's EMR; publish medical device outcomes, such as lab results and other test results, to a patient's EMR; and publish digital media from a device into a patient's EMR, publish infusion data, if required, and infusion events (e.g., infusion rate, volume infused, volume to be infused, rate change, begin bag, end bag) into a patient's EMR.

The application 268 works with the services 260 to facilitate a specific service, such as a patient to device association. The application 268, in one embodiment, may be a user interface, such as the user interfaces illustrated in many of the figures associated with this application. Here, the user interfaces may be screen shots of associating a patient to a device, or to an order, for example. While one application 268 is illustrated in FIG. 2, more than one application is considered to be well within the scope of the present invention. The services 260 and the application 268 are incorporated such that the services 260 retrieve raw data from the main bus 246 and other components, while the application 268 uses that information and presents it to a user through a user interface.

While only a main bus 246 is illustrated in FIG. 2, more than one bus may be used in implementing embodiments of the present invention. By way of example only and not limitation, the main bus 246 may be a first bus that is responsible for managing all of the medical devices. This main bus 246 may be located at the facility, such as a hospital. One or more local busses may be present that can store and facilitate the transfer of information from one or more medical devices, and that transfer that information to the main bus 246. The main bus 246 may not even be aware that there are local busses, as the local busses may just be proxying messages that they receive from the medical devices. Local busses may also be present at the facility (e.g., hospital), but may be physically located in a patient's room, for example, such as on a cart where an associated medical device is located. In one embodiment of the present invention, more than one main bus 246 may be available to provide a backup system. One main bus may be a primary node, and the other may be a secondary node. If one node goes down, the secondary node may be utilized. Additionally, the nodes or busses may be used in conjunction with one another such that each has certain responsibility, for example.

The database 256 may be sent patient, medical device, and order association information. For instance, identification of a patient and medical device that have been associated may be sent to the database 256. Any data that it released by the medical device may also be routed to the database 256 so that this information can be stored in a flowsheet, for example. A clinician may then make the decision as to what to do with the data. For example, the clinician may decide that certain data points should be included in the patient's chart, and the others may be completely deleted from the database 256. A specific example of this may be when a clinician looks at data in the database 256 that is associated with a certain patient. The data may include values at different times, such as 12:00 PM, 12:15 PM, and 12:30 PM. The clinician may not wish for all of these values to be entered into the patient's chart, but may choose, for example, just the 12:00 PM and 12:30 PM entries to officially document. Additionally, having this information in the database 256 allows for a higher accuracy. In one instance, a clinician may write down in a patient's chart that an infusion pump began at 12:10 PM, when it actually started at 12:06 PM. Having this information in the database 256 allows for the clinician to officially document accurate start and end times, as well as other values whose accuracy is important to the patient's health.

As previously discussed, various healthcare providers 254 may wish to receive data or information regarding a particular medical device or patient. In this case, the adapters 240 may be configured to send this information via an HL7 or ASTM connection, for example, to the healthcare providers 254. In one embodiment, the services 260 may communicate with various healthcare providers 254, and this communication takes place via the main bus 246.

Figure 3:
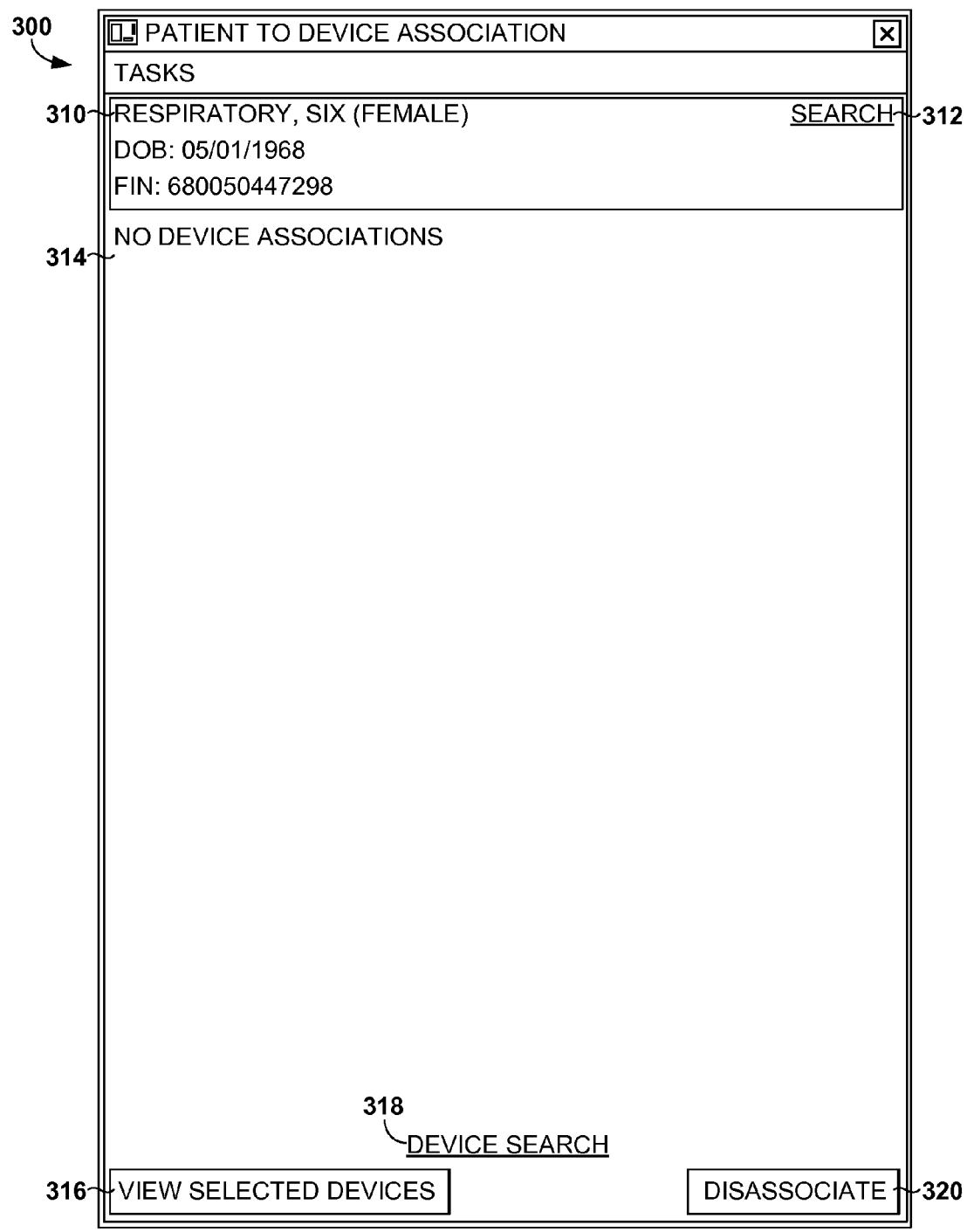
FIG. 3 is an illustrative screen display showing an identified patient, in accordance with an embodiment of the present invention.

Turning now to FIG. 3, an illustrative screen display 300 is shown with a patient having been identified, in accordance with an embodiment of the present invention. Initially, a user, such as a clinician, may wish to associate a patient and a medical device, for example. This association may allow the clinician to continually receive data from the associated medical device for as long as it is associated to the patient. This continuous feed of data may be fed from the medical device to a bus and various components, such as those contained in the device messaging services 212, as shown in FIG. 2. The data may then be sorted, and routed to the appropriate services and applications, such as a patient to device association application, as described herein. Medical devices may include any medical device that could be used to treat a patient, or any devices or mechanisms that may be used by a patient during a hospital stay or doctor's office visit, for example. These medical devices may include, for exemplary purposes only, a patient's bed, monitors (e.g., fetal monitors), pumps (e.g., infusion pump), cardiac ventilators, sequential compression devices, electronic security devices, etc. Further, the association of a patient to a medical device may continue until the occurrence of a disassociation event, which will be described below. The association continues not only when the portable computing device is in the patient's room, but may continue for an extended period of time until a disassociation event occurs.

With continued reference to FIG. 3, a patient has been identified, as shown as patient identification area 310, and various types of patient identification information are displayed, including, but not limited to, the patient's name, gender, date of birth, identification number, and the like. A patient may be identified by a variety of means. For instance, a patient may be identified by scanning a barcode that is located on or near the patient. When a patient is admitted to a hospital, for example, the patient may wear a wristband that has a barcode such that the patient may be easily identified. Alternatively, a patient's bed may have the patient's identification located somewhere on it for quick access. Another form of identification may be used instead of a barcode, such as a patient identification number or other identification form that may be entered into a mobile computing device (e.g., PDA) to identify the patient.

Another option for identifying a patient may include searching a database for a specific patient. The database may include each patient who is currently admitted to the hospital, for example, and thus any patient who is admitted to the hospital may be easily found in the database. A search option is shown as item 312, and may allow a user, such as a clinician, to search for another or a different patient.

Device display area 314 may display any medical devices that have been identified or associated to the patient. As shown here, no medical devices have yet been either identified or associated with the patient identified in patient identification area 310. Similar to that described above in relation to identifying a patient, medical devices may be identified in many of the same ways. For example, a barcode located on or near a medical device, in one embodiment, may be scanned, and information corresponding to that medical device may be uploaded to a mobile or portable computing device for display. Or, an identification number or other identifier corresponding to the medical device may be entered, either manually or electronically, to the portable computing device, for example. Alternatively, and as previously described, a search function may allow a user to search (e.g., by using device search 318) for a specific medical device that is located in a database. A user may view selected devices by selecting item 316, and although these devices may not yet be associated with the identified patient, these devices may be viewed by the user by selecting item 316.

Embodiments of the present invention allow for a clinician to disassociate medical devices that are currently associated to a patient. In one aspect, a clinician may select specific medical devices, and select a disassociate button, such as button 320, and the selected medical devices will be disassociated from the patient. For example, upon a patient checking out of a hospital to return home, the devices that had been used to treat the patient, and thus had been associated to the patient, may be disassociated by the method described above. There are other ways that medical devices may be disassociated from a patient. For instance, a medical device may become disassociated by a patient when another patient becomes associated with that same medical device. This override may take place when a clinician is presented with a dialog box that indicates to the clinician that another patient is associated with that medical device. The clinician may have the option, in some embodiments, to override the existing association. Other methods of disassociating a patient from a medical device will become apparent in the discussion below.

Figure 4:
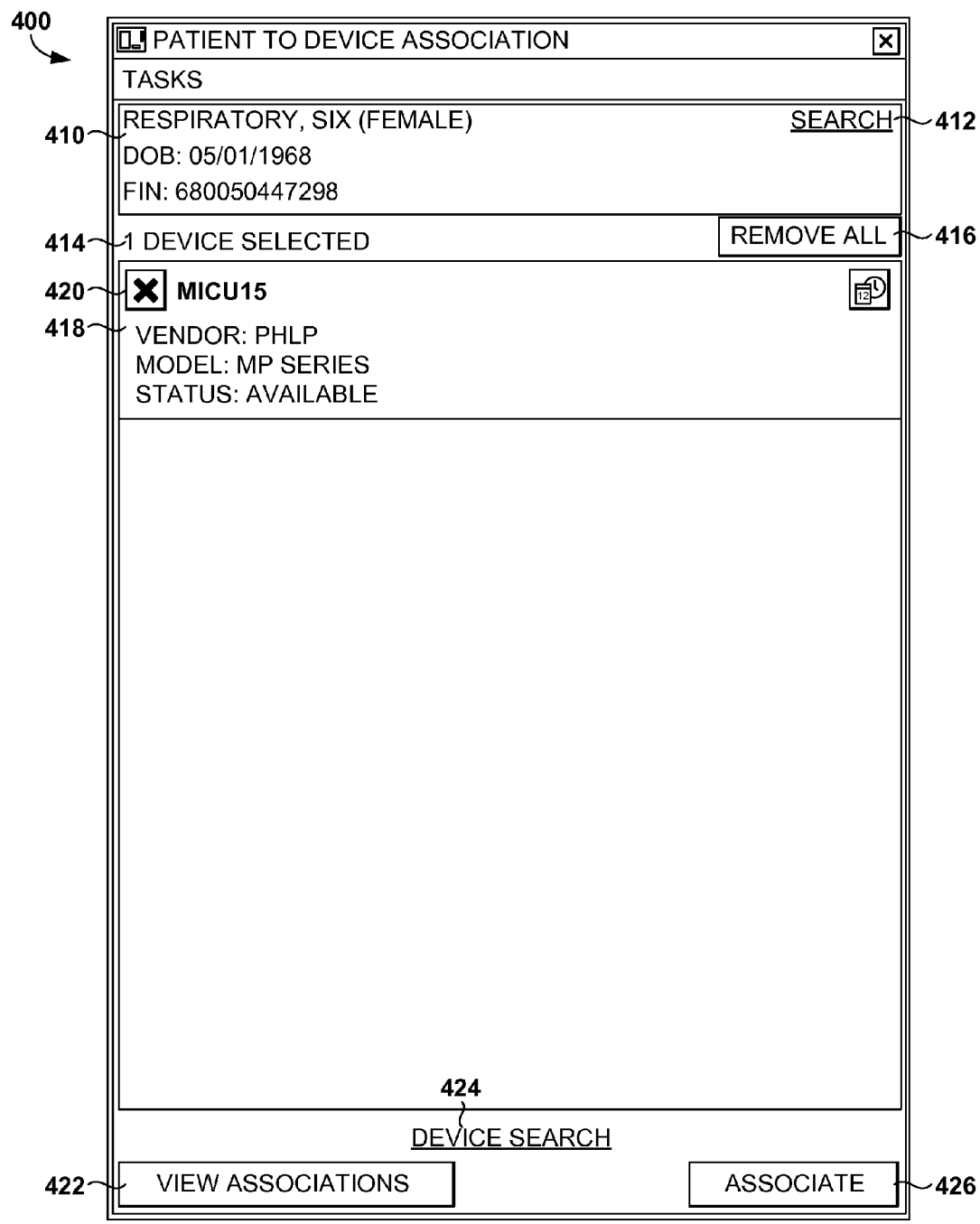
FIG. 4 is an illustrative screen display showing an identified patient and an identified medical device, in accordance with an embodiment of the present invention.

Turning now to FIG. 4, an illustrative screen display 400 is shown with a patient and a medical device having been identified, in accordance with an embodiment of the present invention. Similar to the embodiment of FIG. 3, FIG. 4 includes a patient identification area 410 that includes information corresponding to the patient (e.g., name, gender, date of birth, identification number) who has been identified in the system. The identification of the patient may take place in a variety of ways as described above, such as, but not limited to, scanning a barcode associated with the patient, entering a patient's name or other type of identification, searching for the patient in a database containing a plurality of patient's (e.g., by selecting the search option 412), or the like.

Status area 414 indicates that one device is available for being associated to the identified patient, as the medical device 418 shown in device display area has not yet been associated. Here, various information regarding the identified medical device may be displayed in the device display area, such as, for example, the name of the device, the vendor, the model, and status of the device. If the device is currently associated to another patient, this may be indicated as the status of the application. Here, the device 418 is available, as shown in the device display area. Checkbox 420 allows a user to select that particular device, and either remove it from the screen, associate the device to the identified patient (e.g., by using the associate button 426 once the checkbox 420 is checked), or to disassociate the device from the identified patient, depending on whether the device is currently associated or not. The remove all button 416 allows for a user, such as a clinician, to remove all devices that are selected, such as if the devices have not yet been associated, but have been added as an identified device, as shown here. The view associations button 422 allows a user to view any medical devices that are currently associated to the identified patient. As with the patient, medical devices may be identified by one of many available methods, such as, but not limited to, scanning a barcode associated with the medical device, entering a device's name or other type of identification, searching for the device in a database containing a plurality of medical devices (e.g., by selecting the device search option 424), or the like.

Figure 5:
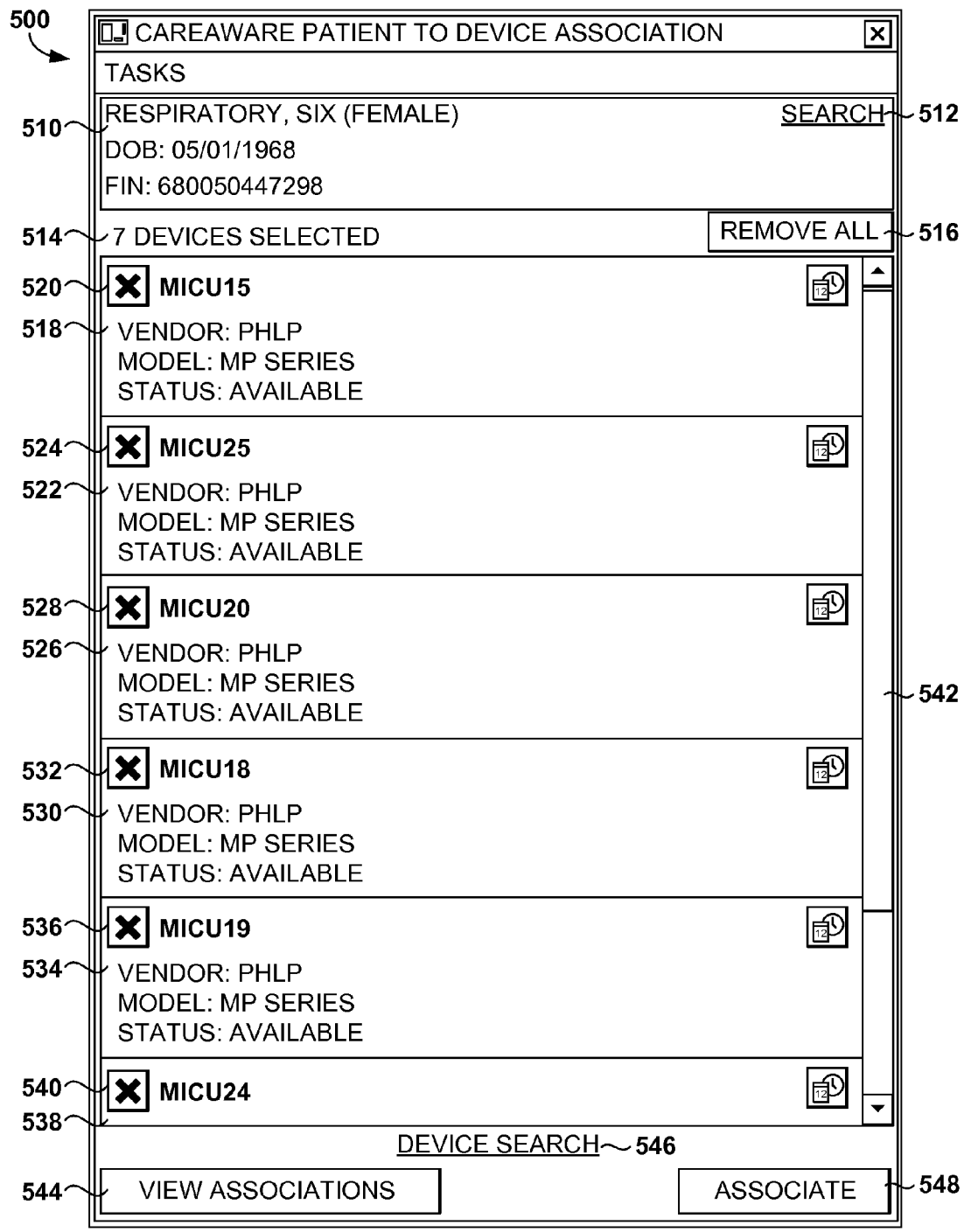
FIG. 5 is an illustrative screen display showing an identified patient and a plurality of identified devices, in accordance with an embodiment of the present invention.

FIG. 5 is an illustrative screen display 500 showing an identified patient and a plurality of identified devices, in accordance with an embodiment of the present invention. Initially, the embodiment of FIG. 5 is similar to that of FIG. 4, except that more than one medical devices are shown as having been identified. Here, a patient has been identified in a patient identification area 510, along with information associated with the patient, such as the patient's name, date of birth, identification number, gender, etc. Other patient information not specifically mentioned here may also be displayed in the patient identification area 510. A patient may be identified by one of several means of identification. For exemplary purposes only and not limitation, these means of identification may include scanning a barcode associated with the patient, entering a patient's name or other type of identification, searching for the patient in a database containing a plurality of patient's (e.g., by selecting the search option 512), or the like.

Status area 514 indicates that there are seven devices that may be associated, upon each device having been checked, using checkboxes 520, 524, 528, 532, 536, 540, etc., and upon a user (e.g., clinician) selecting an associate button 548 located near the bottom of the illustrative screen display 500.

Alternatively, a user may select one or more of the identified devices 518, 522, 526, 530, 534, 538, etc., and may select the remove all button 516 to remove the selected devices from the illustrative screen display 500. As previously described one or more medical devices may be added, or identified, and as such may appear in a device identification area on a screen display. Here, there are more devices identified than can be displayed in the area provided, and as such, a scroll bar 542 may be provided to allow for a user to quickly view medical devices that are not currently displayed in the device identification area.

In one embodiment, the devices are not yet associated until they are selected (e.g., by selecting each checkbox), and then associated. In an alternative embodiment, however, medical devices may be associated upon their identification. For example, a clinician may scan a barcode associated with a medical device. Upon scanning the barcode, the medical device may become automatically associated to the identified patient, instead of requiring the clinician to select the device once it has been identified, and then associating the device (e.g., by selecting the associate button 548). Here, a view associations button 544 is provided to allow a user to view only those medical devices that have been associated to the identified patient, as identified in the patient identification area 510.

Figure 6:
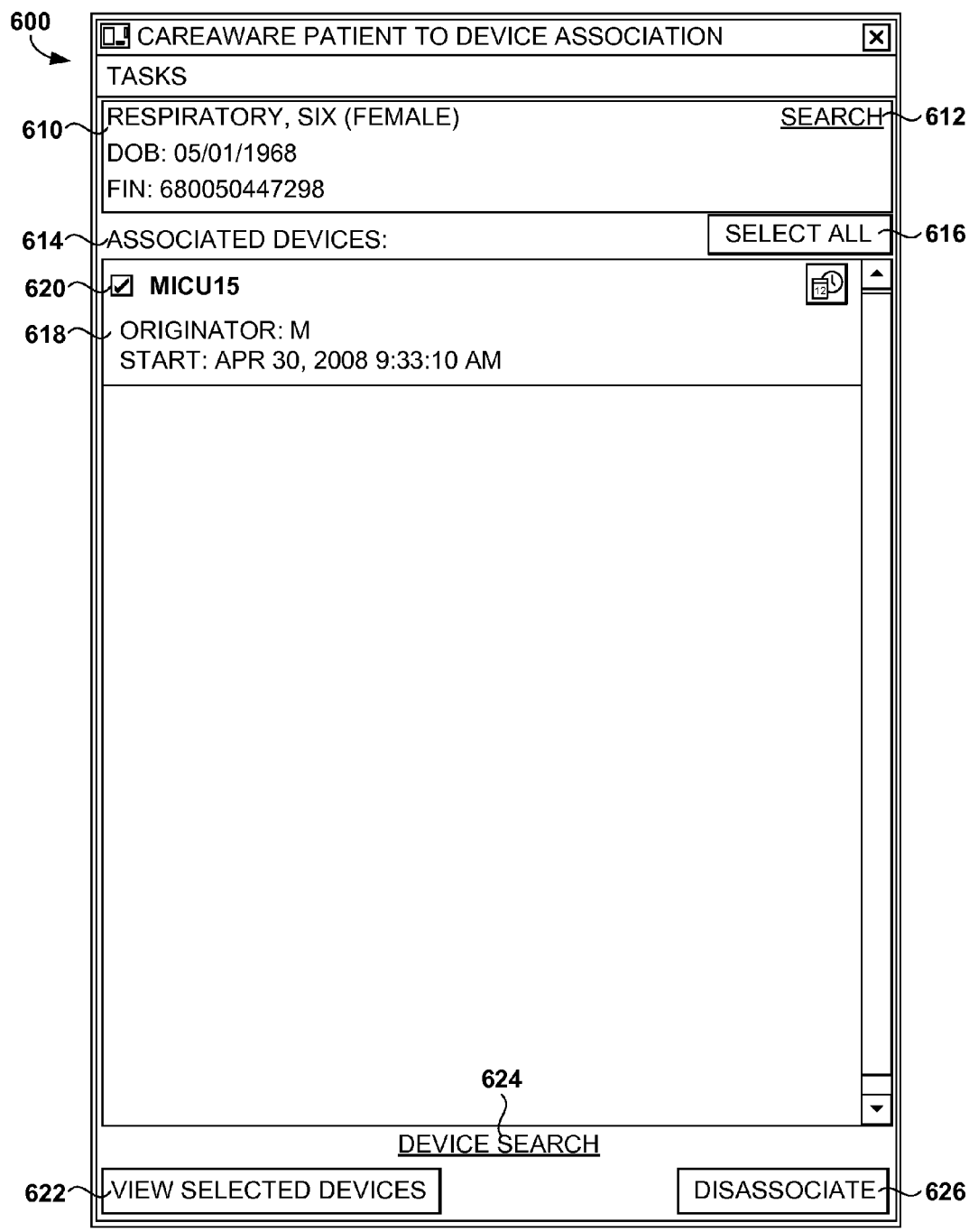
FIG. 6 is an illustrative screen display showing an identified patient and an identified device that has been associated to the identified patient, in accordance with an embodiment of the present invention.

FIG. 6 is an illustrative screen display 600 showing an identified patient and an identified device that has been associated to the identified patient, in accordance with an embodiment of the present invention. A patient has been identified, and various types of identification information for the patient is displayed in the patient identification area 610. A patient may be identified by scanning a barcode associated with the patient, entering some form of identification, or searching for a patient in a database that contains a plurality of patients. This may be accomplished by selecting a search button 612, for example.

Medical devices that have been identified, and perhaps even associated, are displayed in a device identification area. Information that may be useful to a clinician may appear near the identification of the associated device. For instance, this information may include the originator, and the start time, which indicates the time that the device may have been first associated to the patient. This may be useful in that the clinician may go through the stored data for that device and retrieve particular information that may be needed in the future, starting with the time the device was first associated. As will be discussed below, a clinician may be able to retroactively associate a device to a patient, such as if the patient's treatment included the use of a particular medical device before a clinician had the opportunity to associate it.

Here, one device 618 has been associated, as indicated by the status area 614, which states "associated devices." Further, a disassociate button 626 is located near the bottom of the illustrative screen display 600, which allows for a user to select a device (e.g., by selecting checkbox 620) to disassociate it. As a disassociate button 626 is shown on the display and not an associate button, which may assist the user in determining whether the device shown is associated or not. Here, since the disassociate button 626 is shown, the user may understand that the device 618 is already associated since there is not an option to associate the device. Once a device is no longer associated to the identified patient, the device identification may still appear in the device identification area. A remove all button 616 is provided, and allows the user to remove the device from the screen display. Additionally, a view associations button 622 is also located near the bottom of the illustrative screen display 600, which may allow a user to view only those medical devices that are currently associated to the identified patient. In one embodiment, associated devices are always displayed in the device identification area, but in another embodiment, associated devices are not displayed in the device identification area unless the view associations button 622 is selected.

Medical devices may be added or identified by a variety of means, such as, but not limited to, scanning a barcode associated with the device, entering some form of identification for the device into a portable computing device, or searching for the device in a database (e.g., by selecting a device search option 624).

Figure 7:
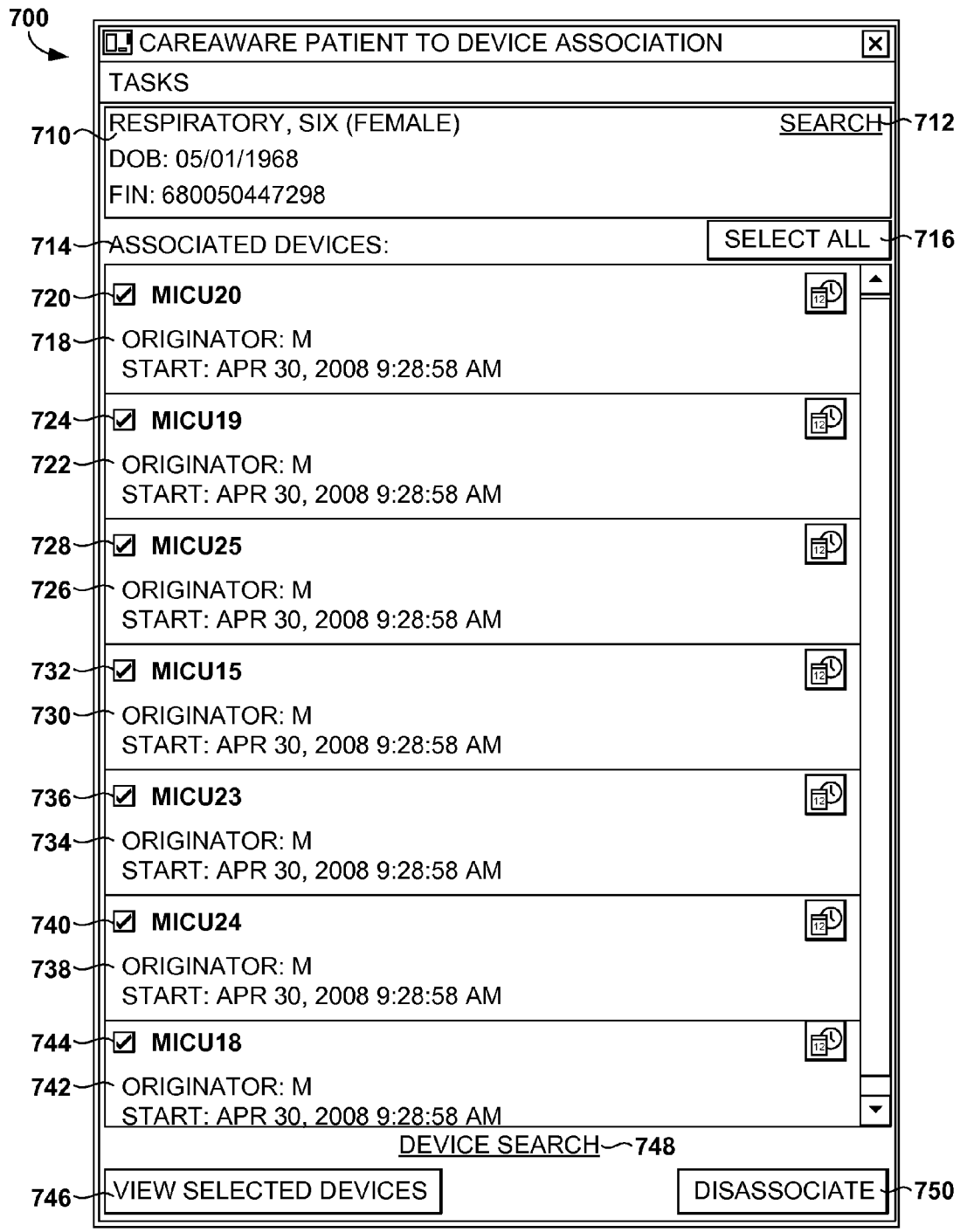
FIG. 7 is an illustrative screen display showing an identified patient and a plurality of identified devices that have been associated to the identified patient, in accordance with an embodiment of the present invention.

Referring now to FIG. 7, an illustrative screen display 700 is shown with a patient and a plurality of devices that have been identified and associated to the identified patient, in accordance with an embodiment of the present invention. Initially, a patient is identified in the patient identification area 710, and may be displayed along with various types of identification information, such as, but not limited to, the patient's name, date of birth, identification number, gender, etc. A patient may be identified by scanning a bar code, a clinician entering some type of identification of the patient into a portable computing device, or by scanning a database for the patient, which may be accomplished by using a search option 712.

Item 714 is a status area that indicates to the user that there are devices that are currently associated to the identified patient. The embodiment of FIG. 7 is similar to that of FIG. 6, except that FIG. 7 illustrates that more than one device may be disassociated at the same time. Here, devices 718, 722, 726, 730, 734, 738, and 742 are the devices that have been identified and associated. There may be more devices that have been identified and associated, but are not displayed on the illustrative screen display because there may not be enough room. In these cases, a scroll bar may be provided, and may act as a positional indicator to indicate to the user that there are more devices than what is shown on the display at any one time. A user may choose to disassociate one or more of the medical devices that are currently associated by selecting the checkboxes 720, 724, 728, 732, 736, 740, 744, etc., of the devices that the user wishes to disassociate, followed by a selection of a disassociate button 750, located near the bottom of the illustrative screen display 700. Once disassociated, these devices may be removed from the display by once again selecting the checkboxes 720 724, 728, 732, 736, 740, 744, etc., of the devices that the user wishes to remove from the display, followed by selecting a remove all button 716.

Medical devices may be identified in much the same way as described for patients, such as by scanning a bar code associated with the device, entering a device identification into a portable computing display, or by searching for a device in a database, which may be accomplished by selecting a device search option 748. The database may contain only those devices located in a particular area of the hospital or doctor's office, or may contain devices located throughout the hospital. Further, only those devices that are associated to the identified patient may be displayed by selecting a view associations button 746, located near the bottom of the illustrative screen display 700. Various buttons and options, while shown in specific locations on the illustrative screen display 700, may be located in other areas of the display. For example, the disassociate button 750 may be located near the top of the illustrative screen display 700 in one embodiment. This is contemplated to be within the scope of the present invention.

Figure 8:
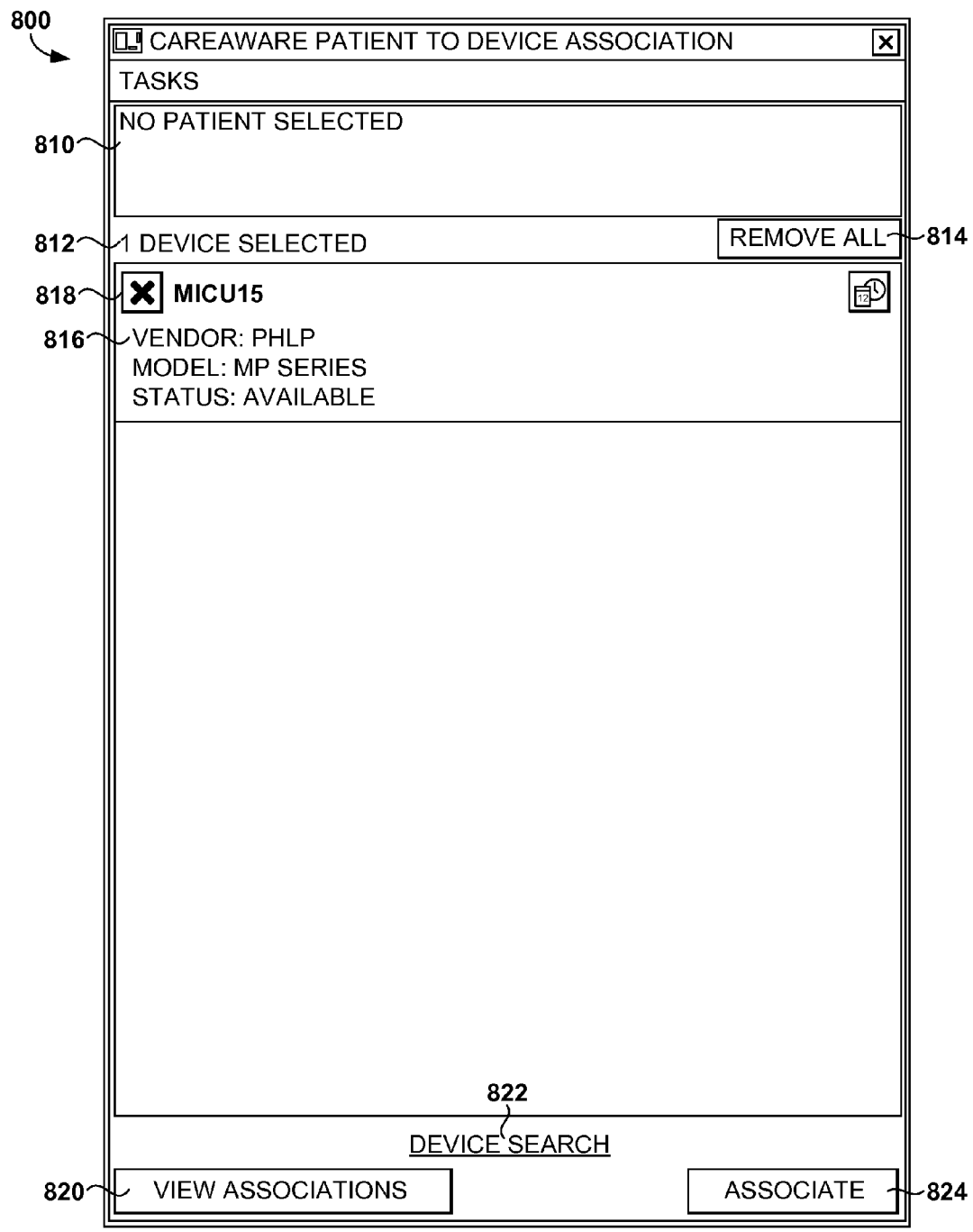
FIG. 8 is an illustrative screen display showing an identified device, in accordance with an embodiment of the present invention.

FIG. 8 is an illustrative screen display 800 showing an identified device, in accordance with an embodiment of the present invention. FIG. 8 is an alternative embodiment to the embodiments described above. Here, a medical device is identified prior to a patient being identified. This scenario may provide advantages to a clinician having to first identify a patient. For example, a patient may be transferred from one hospital room to another, or from a hospital room to the ICU. In either case, if the patient has not yet arrived in the new room or area, the devices may be scanned or otherwise identified prior to the patient entering the room. Then, when the patient enters the new room or area, the patient may be scanned or otherwise identified.

As shown in a patient identification area 810, no patient has been selected. A status area 812 indicates that one device is capable of being associated. This device, device 816 has been selected, as indicated by the checkbox 818. Prior to associating the device, a patient may be identified. Both the device and the patient may be identified in a variety of ways, such as, for instance, scanning a barcode associated with the patient or device, entering an identification that corresponds to the patient or device, or searching for the patient or device in a database. For devices, a device search option 822 may be selected to perform this search. A similar mechanism may be available to search for patients in a database. The database may contain all patients admitted to the hospital, or only those patients located in a certain section. Similarly, the database may contain only those devices located in a certain area of the hospital, or may contain all devices that could be available to the patient (e.g., all devices located in the hospital or surrounding area).

A user may choose to remove the device that has been selected, and may do so, in one embodiment, if the device is not currently associated to a patient. Here, the device cannot be associated, as no patient has yet to be identified. A remove all button 814 may be selected to remove a device that has been selected using the checkbox 818. Further, a view associations button 820 is presented on the illustrative screen display 800, but may not yet be able to be selected, as there currently are no associations. Similarly, an associate 824 button is available near the bottom of the illustrative screen display 800, but in one embodiment, may not be available for selection until a patient has been identified. Alternatively, in another embodiment, the associate button 824 may be available for selection, and may bring up a separate display that prompts the user to select a patient.

Figure 9:
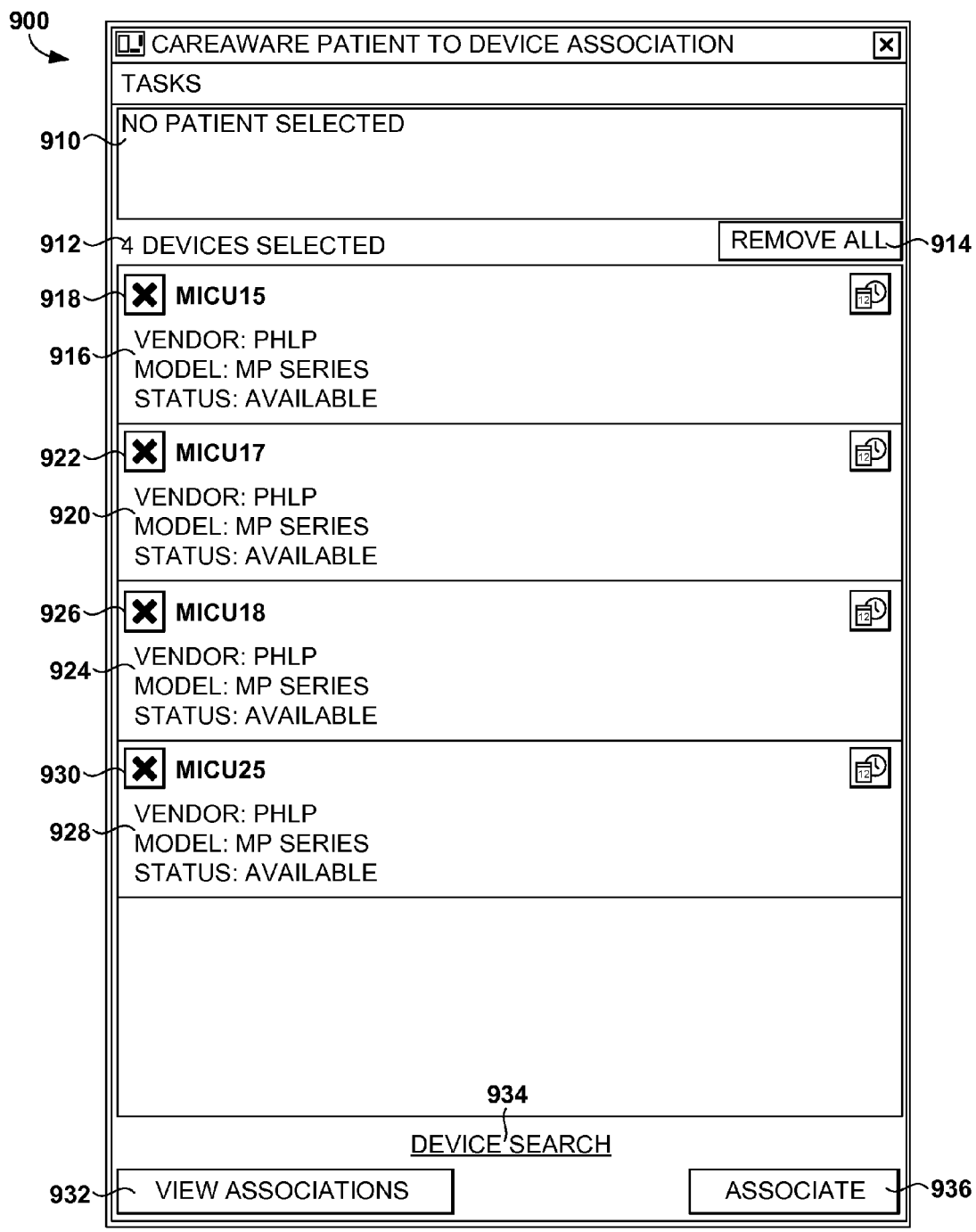
FIG. 9 is an illustrative screen display showing a plurality of identified devices, in accordance with an embodiment of the present invention.

FIG. 9 is an illustrative screen display 900 showing a plurality of identified devices, in accordance with an embodiment of the present invention. The embodiment of FIG. 9 is similar to that of FIG. 8, except that here, more than one medical devices have been identified prior to the identification of a patient. A patient identification area 910 is shown having no patient selected. A status area 912 indicates that four devices are selected, and ready to be associated. Devices 916, 920, 924, and 928 have all been identified, and others may be identified through various means as described above. In one embodiment, a device search option 934 may be selected to allow for a database search for devices. Various information pertaining to each device may also be displayed, such as is shown here. For example, the name of a device, the vendor, the model, and the status may all be shown. Each device has a checkbox 918, 922, 926, and 930, and here, each checkbox has been selected. A user has the option of removing the selected devices from the display by using a remove all button 914, or may identify a patient, and associate the selected devices to the patient. A patient may be selected by, for example, scanning a barcode associated with the patient, entering an identification of the device into a portable computing device or other type of device, or selecting a patient from a database.

A view associations button 932 allows a user to view only those devices that have been associated to the identified device. This button may not be available for selection until a patient has been identified, and one or more associations have been made. As described above, an associate button 936 may allow a user, in one embodiment, to select a patient, and then will associate the selected devices to the identified patient. In another embodiment, however, the associate button 936 may not be available for selection until a patient has been identified.

Figure 10:
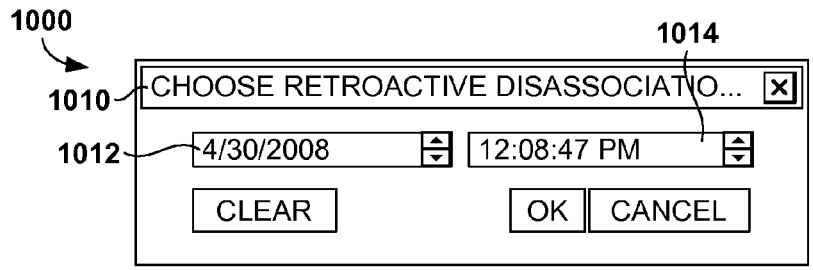
FIG. 10 is an illustrative dialog box that allows a user to retroactively associate or disassociate a medical device, in accordance with an embodiment of the present invention.

FIG. 10 is an illustrative dialog box 1000 that allows a user to retroactively associate or disassociate a medical device, in accordance with an embodiment of the present invention. As briefly mentioned above, a user may have the option to identify a time or date that a device was first associated or disassociated from a particular patient. Here, item 1010 indicates that a user may choose retroactive disassociation, although a similar dialog box may be available for retroactive association. A date box 1012 and a time box 1014 may both be provided. For exemplary purposes only, a user, such as a clinician, may have begun treating a patient using a particular medical device, but may not have associated that device to the patient. Retroactive association allows the clinician to select an accurate time as to when the patient was first being treated using that device, and thus associated to the device. Alternatively, a clinician may cease using a certain medical device in regard to a specific patient, but may not disassociate the patient to device relationship at that point. Retroactive disassociation allows the clinician to go back into the system at a later time, and disassociate the device and patient at the time the association actually should have stopped.

Figure 11:
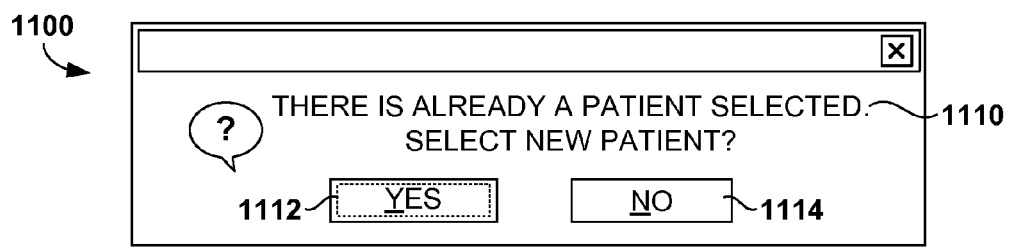
FIG. 11 is an illustrative dialog box indicating that a patient has already been selected, in accordance with an embodiment of the present invention.

FIG. 11 is an illustrative dialog box 1100 indicating that a patient has already been selected, in accordance with an embodiment of the present invention. This type of dialog box may appear if a user attempts to select a patient, when a patient has already been selected. A user may do this if he or she wishes that a different patient be identified so that the different patient can be associated to one or more devices. When this happens, a dialog box similar to the illustrative dialog box 1100 may appear. The box indicates that a patient is already selected at item 1110, and provides a yes button 1112 option and a no button 1114 option. By selecting the yes button 1112, the new patient will be the identified patient in a screen display, such as that shown in FIG. 3, for example, and the patient who was previously identified may be removed from the screen. By selecting the no button 1114, the current patient will remain the identified patient.

Figure 12:
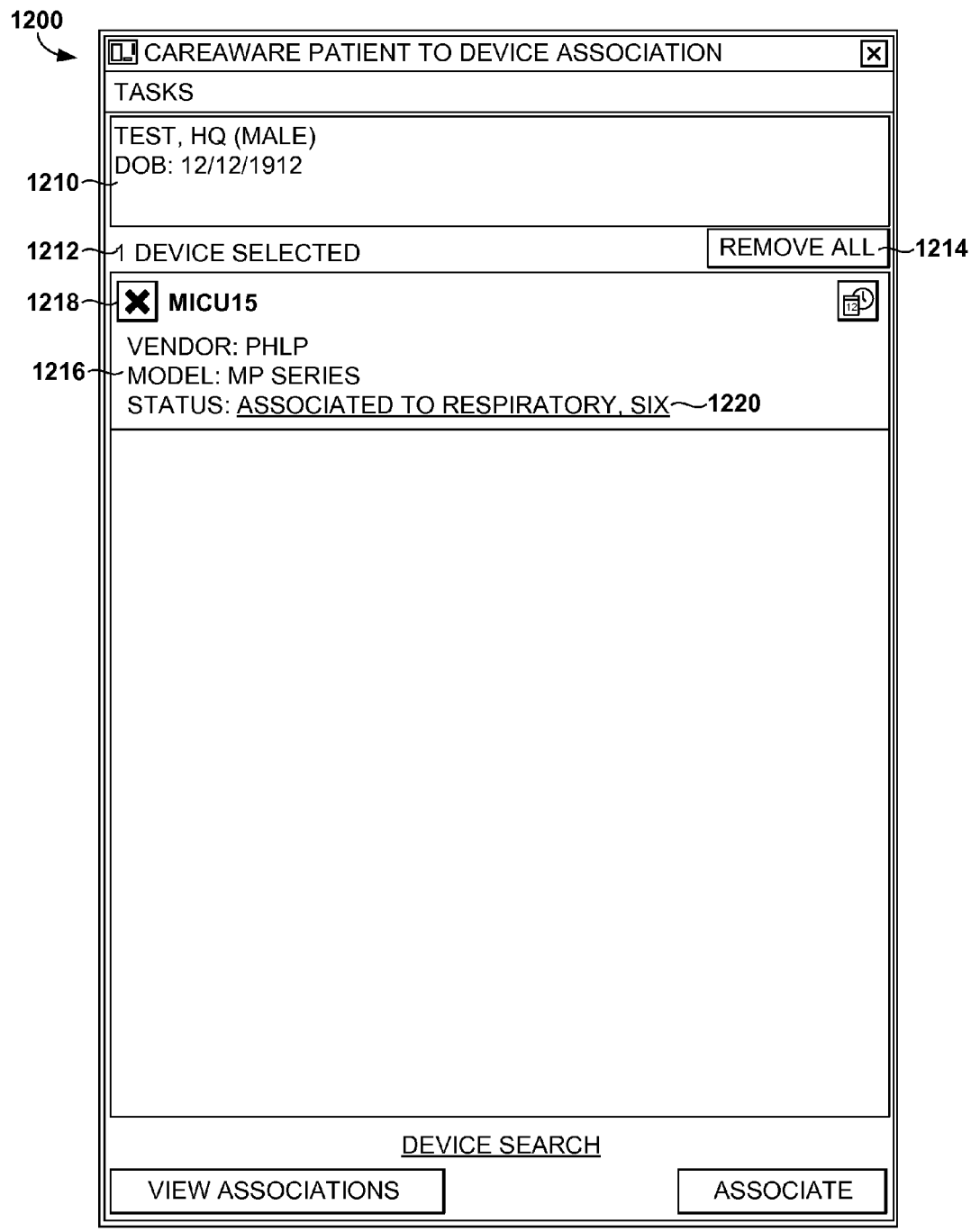
FIG. 12 is an illustrative screen display showing an identified patient and an identified device, in accordance with an embodiment of the present invention.

Turning now to FIG. 12, an illustrative screen display 1200 is shown with a patient and a device having been identified, in accordance with an embodiment of the present invention. Initially, a patient has been identified in a patient identification area 1210. Further, status area 1212 indicates that there is one device that is capable of being associated. Like previous examples, device 1216 includes various types of information related to the device, and also includes a checkbox 1218, which is shown as being selected. A user may remove the device from the display by selecting a remove all button 1214. Here, the status 1220 indicates that the device 1216 is already associated to another patient, named Respiratory, Six. If the user attempts to associate the device 1216 to the identified patient, a dialog box, similar to that shown in FIG. 13, as described below.

Figure 13:
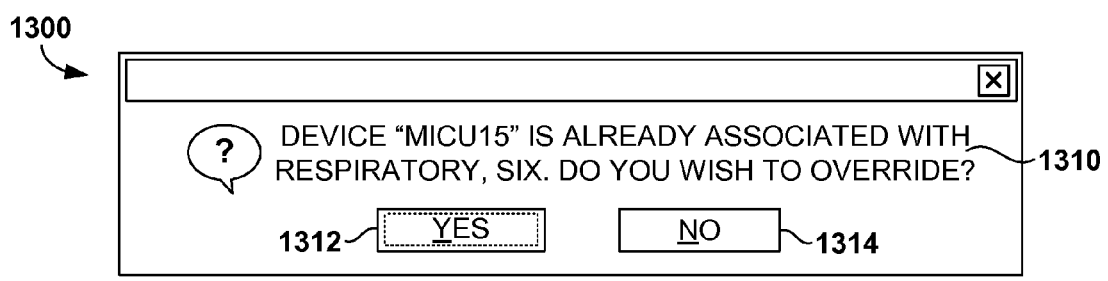
FIG. 13 is an illustrative dialog box indicating that a device is already associated with another patient, in accordance with an embodiment of the present invention.

FIG. 13 is an illustrative dialog box indicating that a device is already associated to another patient, in accordance with an embodiment of the present invention. As previously described, a user may attempt to associate a patient with a particular medical device that is currently associated to another patient. In this case, a dialog box similar to that shown in FIG. 13 may appear, and may indicate that another patient is already selected, such as is shown by item 1310. Item 1310 may also include a question as to whether the user wishes to override the existing association. The user has the option of selecting a yes button 1312, or a no button 1314. By selecting the yes button 1312, a new association may override the existing association between the medical device and the patient who is currently associated with that device. By selecting the no button 1314, the existing association is kept, and the new association is not made.

Figure 14:
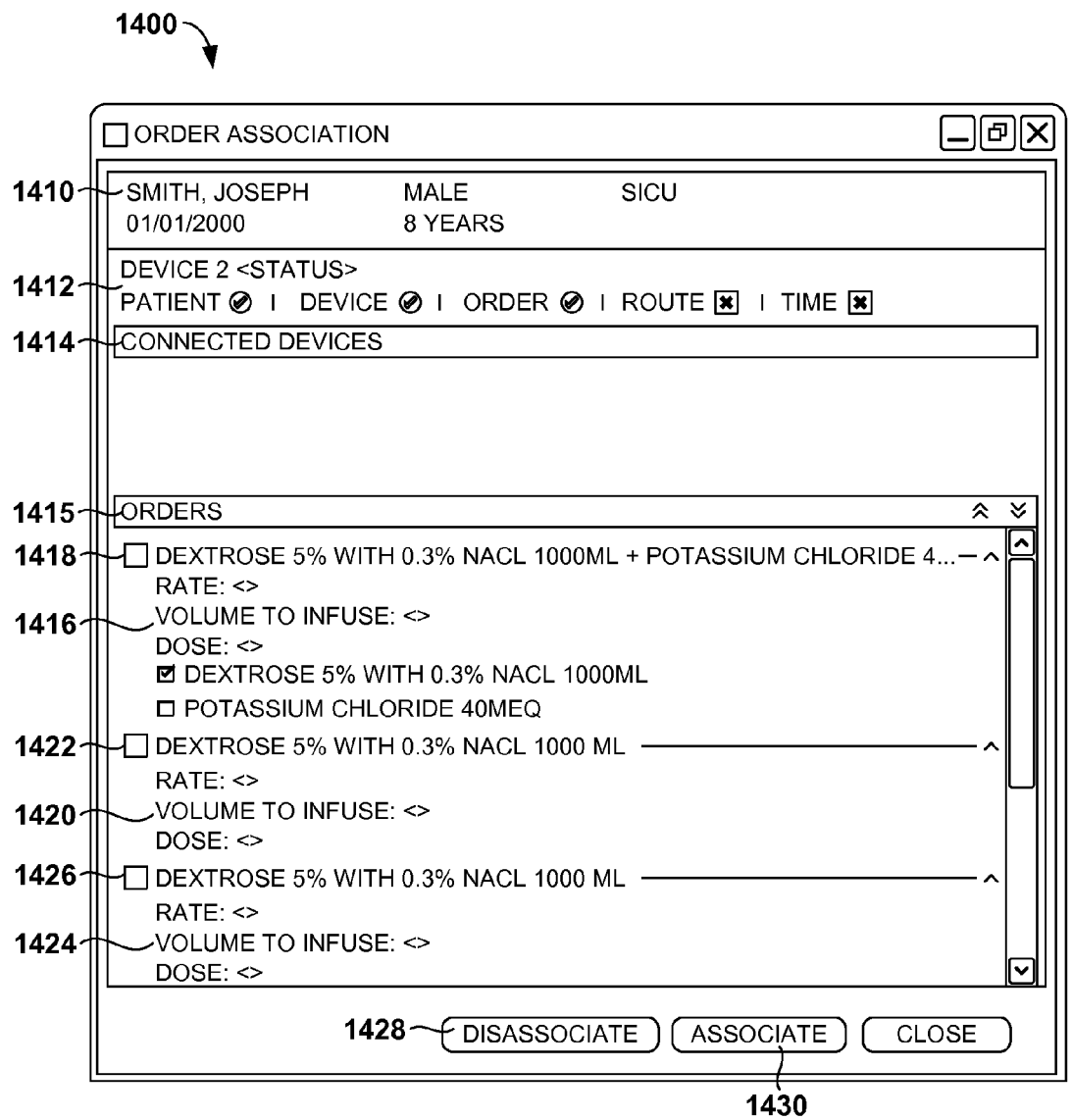
FIG. 14 is an illustrative screen display showing a selected patient and a plurality of orders, in accordance with an embodiment of the present invention.

Turning now to FIG. 14, an illustrative screen display 1400 is shown having a selected patient and a plurality of orders, in accordance with an embodiment of the present invention. Initially, some medical devices may be capable of being associated with orders, such as an order from a caregiver who is authorized to prescribe or to give orders. An exemplary order may be to give a patient 1000 mL of dextrose 5% with 0.3% NaCl. The type of order may very depending on the type of medical device that is required to carry out the order.

A patient identification area 1410 identifies the patient, and gives other information regarding the patient, such as the patient's name, birth date, gender, age, etc. A device identification area 1412 identifies a medical device, and may also provide certain information about the device, as shown in the device identification area 1412. Item 1414 indicates that connected devices may be listed below. Here, there are no connected devices, as the device identified in the device identification area 1412 may not have been associated to the patient at the current time. Item 1415 indicates that orders may be listed below. Here, orders 1416, 1420, and 1424 are able to be seen on the display, although more may be accessible using a scroll bar, for example. In one embodiment, each order shown on the display may correspond to the patient identified in the patient identification area 1410. In most cases, orders are made for an individual patient, and may be carried out only for that patient and not any other patient. Therefore, if a patient has already been identified, such as is the case in the embodiment of FIG. 14, the orders that are shown may be only those that have been made for that patient.

Orders 1416, 1420, and 1424 each have a checkbox, numbered 1418, 1422, and 1426, of which may be selected to perform different functions. In one instance, one or more orders may be selected and removed from the display. In another instance, if an order is currently associated, it may be selected and disassociated by selecting a disassociate button 1428. Alternatively, if an order is not currently associated, it may be selected and associated by selecting an associate button 1430. It should be noted that not all devices may require an order. For example, monitors, cardiac ventilators, balloon pumps, a patient's bed, and other stationary devices may not require orders in order to be associated and used to treat a patient. On the other hand, devices such as, for example, infusion pumps, sequential compression devices, and electronic security devices may require an order from an authorized caregiver in order to be used in association with a patient.

Adding the capability to associate an order, and therefore a patient, with a medical device, may greatly increase the level of accuracy in many respects. For example, a clinician, when executing an order, such as giving 1000 mL of dextrose 5% with 0.3% NaCl to a patient by way of a pump, may write down a start time according to the clinician's watch. The watch, however, may not be synched to the time kept by the system. If there is an association made between the order and the device, the exact start and end time will be kept in the system for that patient, and most or all inaccuracies will disappear. Further, having the capability of associating an order to a device allows for a much simpler method of searching for specific information. For example, if a clinician wishes to search for information on a certain device that has been used to treat a particular patient, the clinician need only to locate the association of the order to the device, or even if it is an association of a patient to a device, and the information that the clinician needs is likely to be found in one spot.

Figure 15:
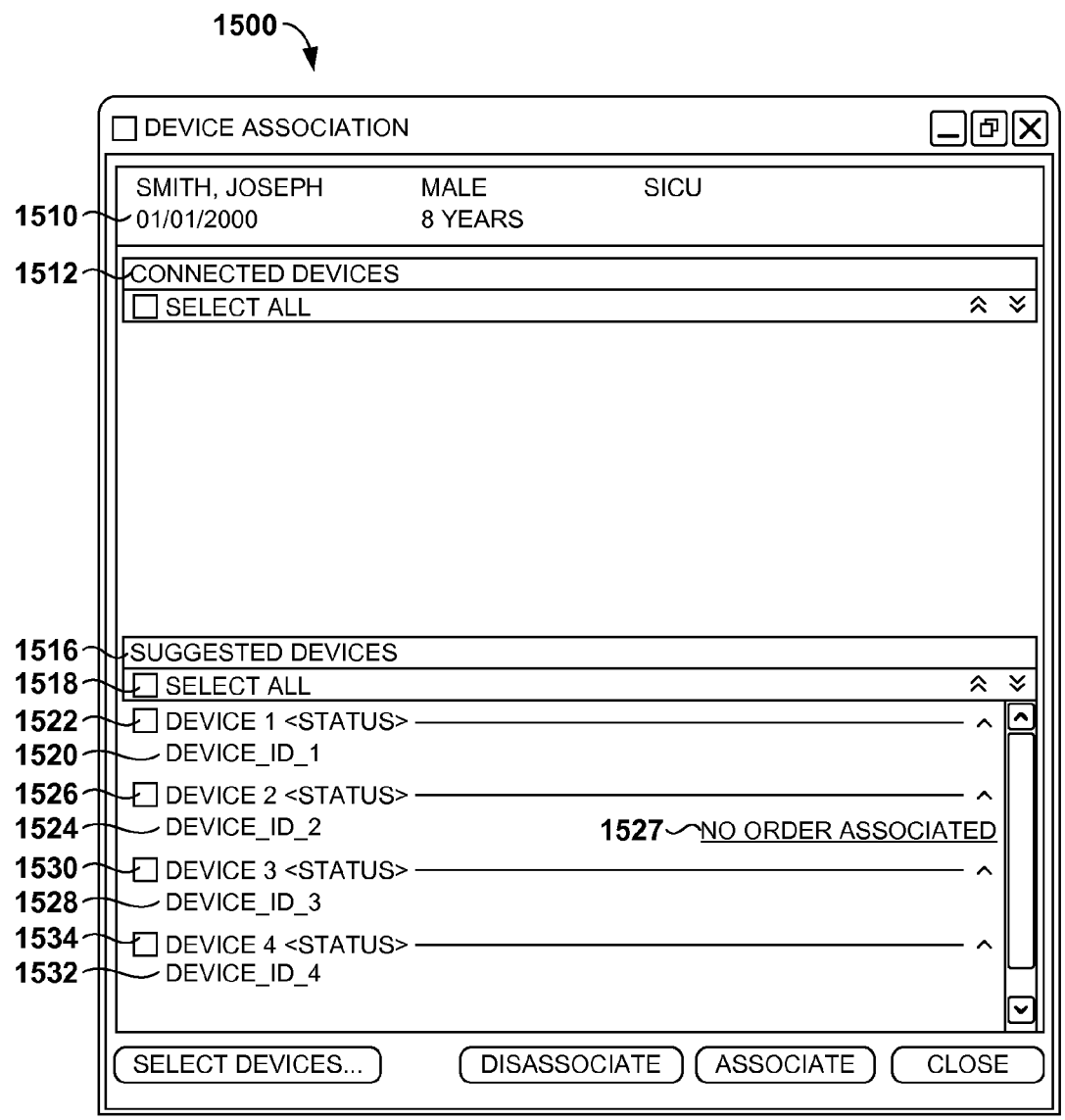
FIG. 15 is an illustrative screen display showing a selected patient and a plurality of suggested devices, in accordance with an embodiment of the present invention.

FIG. 15 is an illustrative screen display 1500 showing a selected patient and a plurality of suggested devices, in accordance with an embodiment of the present invention. A patient identification area 1510 allows for the identification of a patient with various information such as, but not limited to, the patient's name, date of birth, gender, age, and in some embodiments, an identification number or code. Status area 1512 indicates that connected devices are shown below. Here, there are no devices that have been connected, or that have been associated to the patient identified in the patient identification area 1510. Suggested devices area 1516 indicates that several devices have been suggested. Devices may be suggested based on one of many factors. For exemplary purposes only, these factors may include demographics of the patient (e.g., age, gender, weight), the diagnosis or treatment plan of the patient, the location of the patient (e.g., whether patient is in a hospital room, intensive care unit, or other area of a hospital), or the order that has been given or prescribed to the patient. Other factors for suggesting devices are contemplated to be included within the scope of the present invention.

Devices 1520, 1524, 1528, and 1532 are the devices that have been suggested, in accordance with the identified patient. As described above, the devices may have been suggested based on one of the factors listed above. For example, based on the patient being eight years old, certain devices may be better suited for children. Alternatively, because the patient has been admitted to the ICU, certain devices that are used in the ICU may be suggested, as the patient would be in that location or portion of the hospital. As another example, the patient's condition may be such that certain devices are well known, or typically used to treat that condition. These devices may be suggested for use for this particular patient, and for that particular condition. Each device has a checkbox, items 1522, 1526, 1530, and 1534, and these checkboxes may be selected individually to perform certain functions (e.g., to associate or disassociate the devices), or may be selected all at the same time by selecting a select all checkbox 1518.

Item 1527 indicates that an order has not yet been associated with device 1524. As shown, devices 1520, 1528, and 1532 do not have similar indications as indication 1527. This may be for one of many reasons. Devices 1520, 1528, and 1532 may already have orders associated with them, but alternatively, devices 1520, 1528, and 1532 may be devices that do not require orders, such as monitors, ventilators, certain pumps, a patient's bed, or other certain stationary devices.

FIG. 16 is an illustrative screen display 1600 showing a selected patient, a selected medical device, and a plurality of orders, in accordance with an embodiment of the present invention. As mentioned, item 1527 in FIG. 15 indicated that an order has not been associated with device 1524. In one embodiment, item 1527 may be selectable, and when selected, a display, such as that shown in FIG. 16, may be presented to the user. Illustrative screen display 1600 provides a user with several orders that are appropriate given the device (i.e., device 1524 of FIG. 15) that was previously selected, or that is associated with item 1527 in FIG. 15.

A patient identification area 1610 includes information about the patient, such as the patient's name, date of birth, age, gender, and may even contain the location of the patient within the hospital or doctor's office, and an identification number that uniquely identifies the patient. The patient may be identified by any of the methods described herein, including, but not limited to, scanning a barcode associated with the patient, entering a patient identification into a computing device, such as a portable computing device or PDA, or by searching for the patient in a database that contains a plurality of patients. Here, connected devices 1614 indicates that although device 1612 has been identified, it has not yet been connected, or associated. Item 1616 indicates that suggested orders are shown below area 1616. Here, several orders may be suggested based on the patient and identified device 1612, but those that are displayed include orders 1618, 1622, and 1626. A scroll bar may indicate that more orders are available for viewing upon movement of the scroll bar. Each order includes a checkbox 1620, 1624, and 1628, each of which allows a user to select the order to associate it, disassociate it, or make other selections that may be available.

Each order shown may be accompanied by relevant information that corresponds to the order, and this information depends on the type of order that is given. Here, orders 1618, 1622, and 1626 include information regarding a rate, volume to infuse, and a dose. Additionally, orders that may include several components or ingredients (e.g., dextrose with NaCl, and potassium chloride), a user, such as a clinician, may have the option of choosing which ingredients to infuse at a particular time. Although the order, such as order 1618, may have two ingredients, a clinician may be responsible for making the decision as to which ingredients should be included initially, and which may be added at a later time. Here, dextrose 5% with 0.3% NaCl 1000 mL is listed as a separate ingredient from potassium chloride 40 mEq, allowing the clinician to decide which ingredients are appropriate at a specific time. In one embodiment, primary ingredients may not be capable of being selected or unselected by a user, but secondary ingredients may always be capable of being selected or unselected by a user. The primary ingredient may be the most important, and main ingredient, but the secondary ingredient may be optional, or may be required for only a portion of time.

Figure 17:
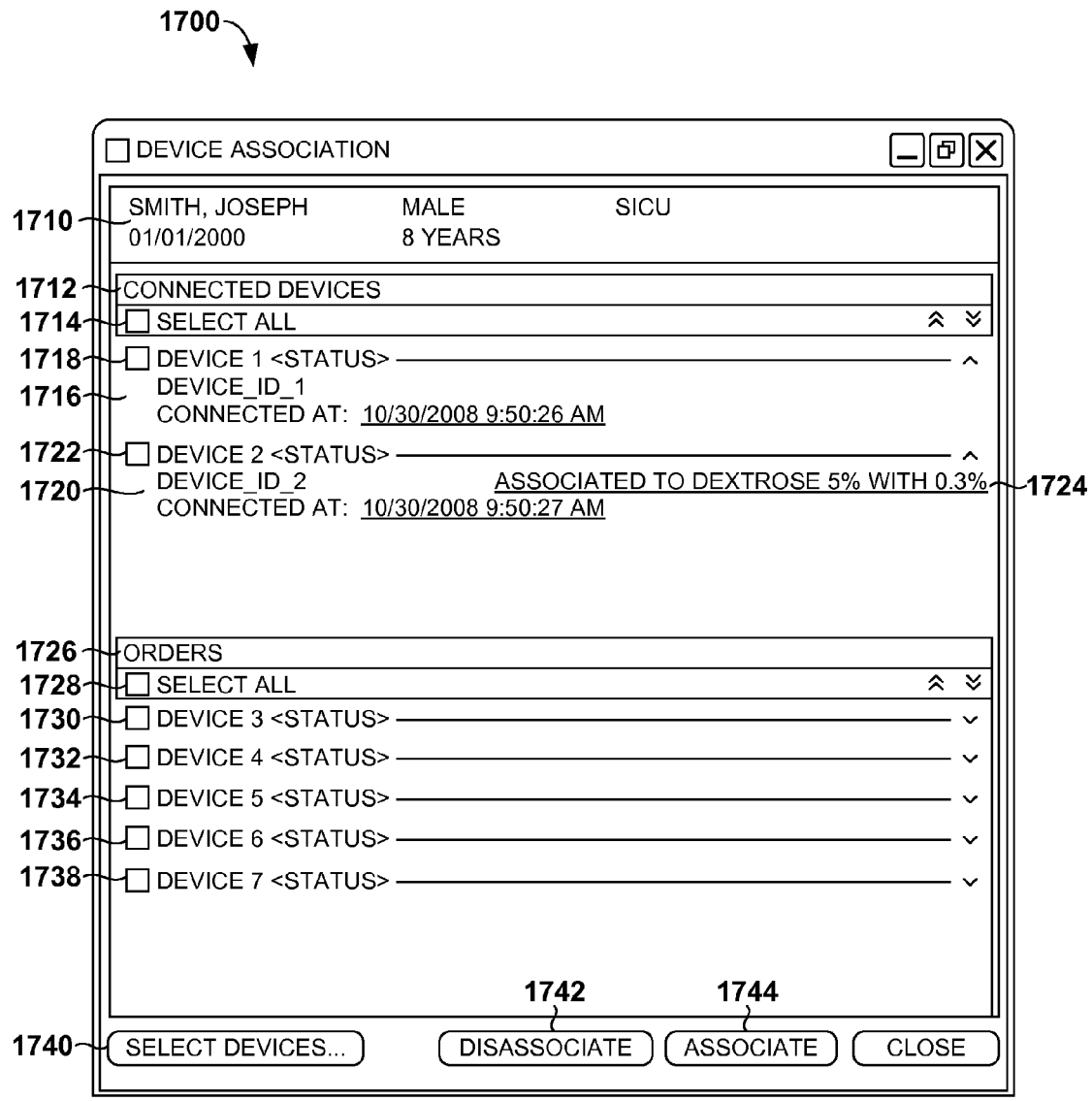
FIG. 17 is an illustrative screen display showing a selected patient, a plurality of suggested devices, and devices that have been associated to the patient, in accordance with an embodiment of the present invention.

Referring now to FIG. 17, an illustrative screen display 1700 is shown having a selected patient, a plurality of suggested devices, and devices that have been associated, in accordance with an embodiment of the present invention. Similar to previously described embodiments, the embodiment of FIG. 17 includes a patient identification area 1710 that may identify the patient (e.g., by name, date of birth, gender, age, location in hospital, identification number). Under connected devices 1712, devices 1716 and 1720 are shown, and as such, may have been associated to the patient identified in the patient identification area 1710. A select all checkbox 1714 may be available to allow a user to select all devices at the same time. A similar select all checkbox 1728 is located beneath orders 1726. Alternatively, each device has its own checkbox, shown as items 1718, 1722, 1730, 1732, 1734, 1736, and 1738, which may be selected individually rather than a select all function. A disassociate button 1742 and an associate button 1744 may be selected upon a selection of one or more devices to either disassociate or associate those devices from the identified patient.

Returning to the connected devices, each device identification may contain pertinent information, such as a device name, a device identification, and a status of the device, which may include a time that the device was connected or associated to the identified patient. Further, devices that may have an associated order may include an indication, such as indication 1724. Item 1724 allows a clinician to glance at the device listed under connected devices 1712 and determine that device 1720 has already been associated to an order, and that the association does not need to be made. In one embodiment, a user may be able to hover a mouse, for example, over an item, such as item 1724, to view details about the item. Here, hovering over item 1724 would allow for a user to view details about the order that is associated with device 1720.

Figure 18:
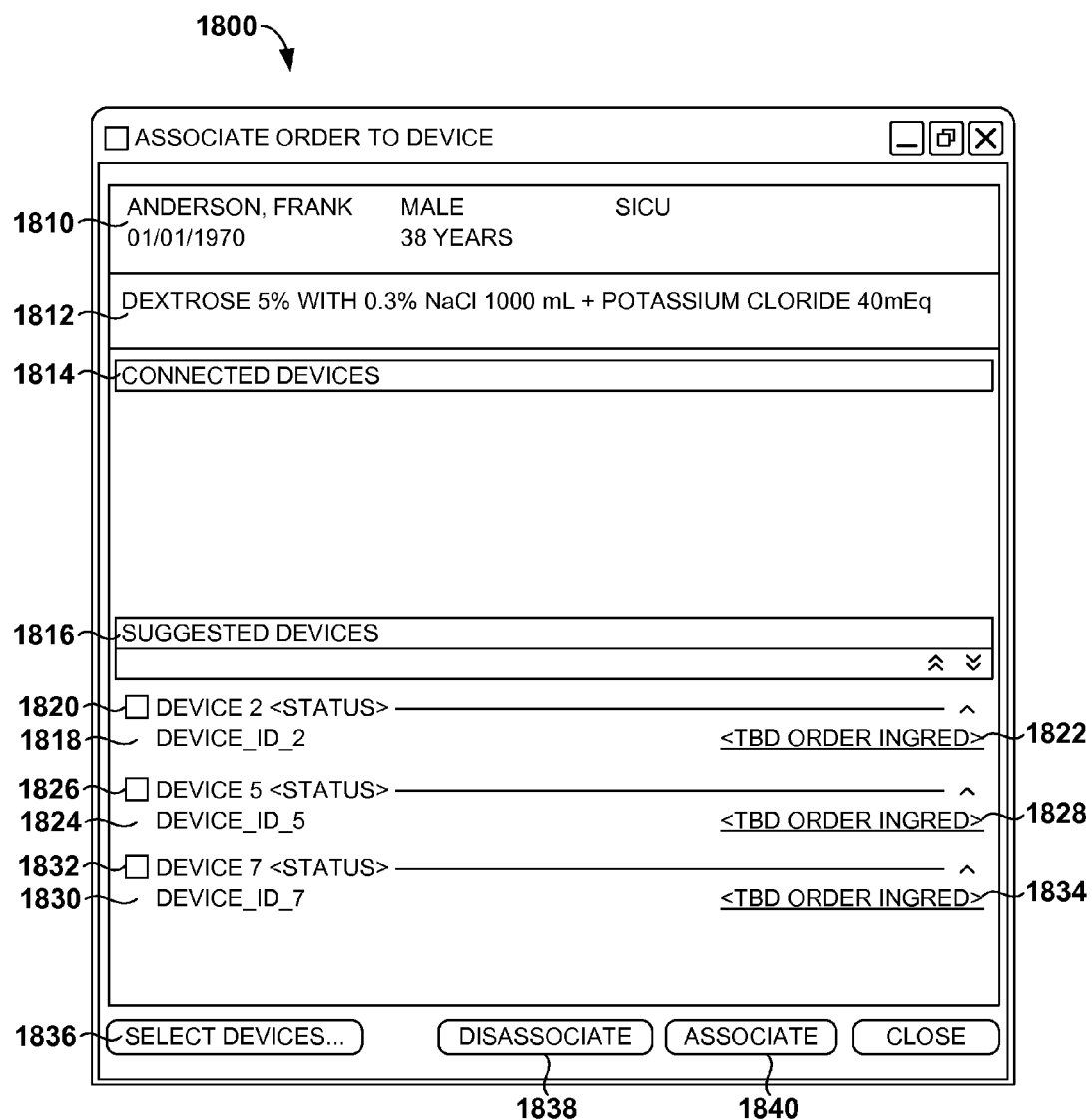
FIG. 18 is an illustrative screen display showing a selected patient and a plurality of suggested devices, in accordance with an embodiment of the present invention.

FIG. 18 is an illustrative screen display 1800 showing a selected patient and a plurality of suggested devices, in accordance with an embodiment of the present invention. A patient has been identified in a patient identification area 1810, and an order 1812 has been identified as well. Beneath connected devices 1814, no devices are currently connected (e.g., associated) to the order and patient identified above. Beneath suggested devices 1816, three devices, devices 1818, 1824, and 1830, have been suggested based on the order 1812. As previously discussed, devices may be suggested, in one embodiment, based on an order. For example, the order 1812 may require an infusion pump. Three infusion pumps may be available in the hospital, or may even be available in the vicinity of the patient's location within the hospital. Each of the three devices 1818, 1824, and 1830 has a checkbox, items 1820, 1826, and 1832, which allows a user to select one or more devices and perform various functions, such as to disassociate the device (e.g., using a disassociate button 1838), associate the device (e.g., using an associate button 1840) or the like. Further, a select devices button 1836 allows a user to select all of the devices without requiring the user to select each device individually.

Each device 1818, 1824, and 1830, in the embodiment of FIG. 18, includes a TBD order ingredient option, which is marked as items 1822, 1828, and 1834. These options alert a clinician that the identified order has multiple ingredients or components, and that one or more ingredients are available for selection. As discussed above, one aspect of the present invention is that a primary ingredient(s) may be unavailable for selection, but secondary ingredients may be capable of being selected or unselected by a user, as secondary ingredients may not be required for the entire time that the primary ingredient is given to the patient.

Figure 19:
FIG. 19 is an illustrative screen display showing a selected patient and an associated order with listed order ingredients, in accordance with an embodiment of the present invention.

FIG. 19 is an illustrative screen display showing a selected patient, an associated order, and a plurality of suggested devices, in accordance with an embodiment of the present invention. Options 1822, 1828, and 1834 shown in FIG. 18 may be selected by a user. Upon selection of one of these options, a display similar to that shown in FIG. 19 may be presented. Various ingredients that comprise the order are displayed, along with checkboxes for each. Here, there are four separate and distinct ingredients, shown as items 1910, 1912, 1914, and 1916. One or more ingredients may be selected. Further, different ingredients may be selected at another time, to allow for flexibility and accuracy in a patient's treatment. For instance, while ingredient 4 1910 may be the only ingredient that is infused at the current time, potassium chloride 40 mEq 1914 may be selected, in addition to ingredient 4 1910, at a later time, and may also be infused.

Figure 20:
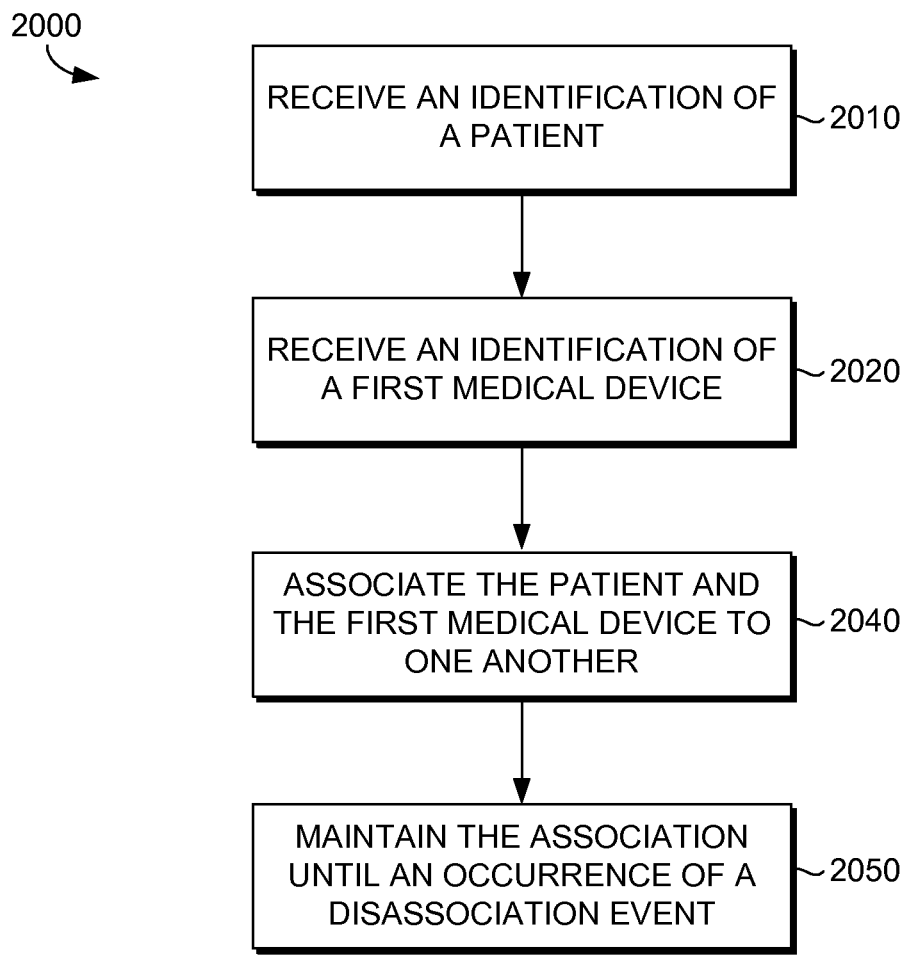
FIG. 20 is an illustrative flow diagram of a method for associating a patient to one or more medical devices, in accordance with an embodiment of the present invention.

FIG. 20 is an illustrative flow diagram 2000 of a method for associating a patient to one or more medical devices, in accordance with an embodiment of the present invention. Initially, an identification of a patient is received at step 2010. As previously described, a patient's identification may be received in one of many ways. For exemplary purposes only and not limitation, a patient may be identified by scanning a barcode located on or near the patient. Alternatively, an identification corresponding to the patient (e.g., identification number, patient's name) may be entered into a computer device, such as a PDA or some other type of portable computing device). In one aspect of the present invention, a database containing a plurality of patient identifications may be searched by a user to locate a particular patient. The database may contain only those patients located in a certain portion of a hospital, or may contain a broader range of patients, such as any that have been checked into the hospital, for example. Further, the database, in one embodiment, is an electronically searchable database.

At step 2020, an identification of a first medical device is received, and at step 2030, an identification of a second medical device is received. Medical device identification may be received in the same way as patient identifications, as outlined above. For example, a barcode associated with the device may be scanned, identification information for the device may be entered into a computing device, a device may be searched for in a database, or the like. In response to receiving the identifications of the patient and the first and second medical devices, the patient and the first medical device may be associated to one another at step 2040. Once an association has been formed between the patient and the first medical device, data from the first medical device may be continuously routed to a data store, where associations and related data are stored. At step 2050, the association of the patient and the first medical device is maintained until the occurrence of a disassociation event. While the association is maintained, as previously mentioned, data from the first medical device may be continuously routed and saved in a data store, such as, for example, data store 264 in FIG. 2. Data routed from the medical devices to the data store may be routed by a bus, such as main bus 246, also in FIG. 2.

In one embodiment, a disassociation event may occur by a clinician disassociating the device from a patient (e.g., selecting the device by scanning it or selecting the checkbox, and selecting a disassociate button on a screen display). This may also be done by the selection of a patient and a device (e.g., selected by scanning a barcode or selecting a checkbox), followed by a clinician selecting a disassociate button on a screen display. Alternatively, more than one device may be disassociated at the same time. As previously described, a select all button may be available if it is desired that all of the devices be selected.

In another embodiment, an indication may be received that a device that is currently associated to a patient has gone offline. One mechanism for determining whether a device is online or offline is a device heartbeat, which is described in relation to FIG. 2. A device heartbeat is a message sent from the device to device messaging services 212 in FIG. 2, for example, that indicates that the device is online. If this device heartbeat is not received for a certain, and perhaps predetermined period of time, it may be determined that the device is offline.

In yet another embodiment, a user (e.g., clinician) may choose to override an existing association between another patient and a medical device so that a new patient is associated with the device. As described in relation to FIGS. 12 and 13, a user may be provided with an alert or notification when a device is identified that is already associated with another patient. If the user chooses to override the existing association, that association will be terminated in favor of a new association with a new patient.

As previously mentioned, more than one medical device may be associated to a particular patient. For instance, the second medical device whose identification was received at step 2030 may also be associated to the patient, while the first medical device is also associated to the same patient. This association may also be maintained until the occurrence of a disassociation event, as discussed above. Further, a third medical device's identification may be received and may then be associated to the identified patient. This association may also be maintained or continued until the occurrence of a disassociation event. If, however, it is determined that any of the medical devices are associated with another patient, an option to override the existing association may be presented on a display device. If an indication of an override is received, the device and patient may be associated to one another, thus terminating the existing association.

As has been previously described, an order may also be associated to a medical device. An order may inherently belong to a particular patient, and thus association may not be required. If that is the case, the order may be associated to a medical device. An identification of an order may be received, such as by scanning a barcode corresponding to the order, entering an identification of the order into a computing device, or searching for an order in a database. Irrespective of which method is used to identify an order, it should be noted that more than one order may be identified and received. A medical device may then be associated to one or more of the identified orders.

Figure 21:
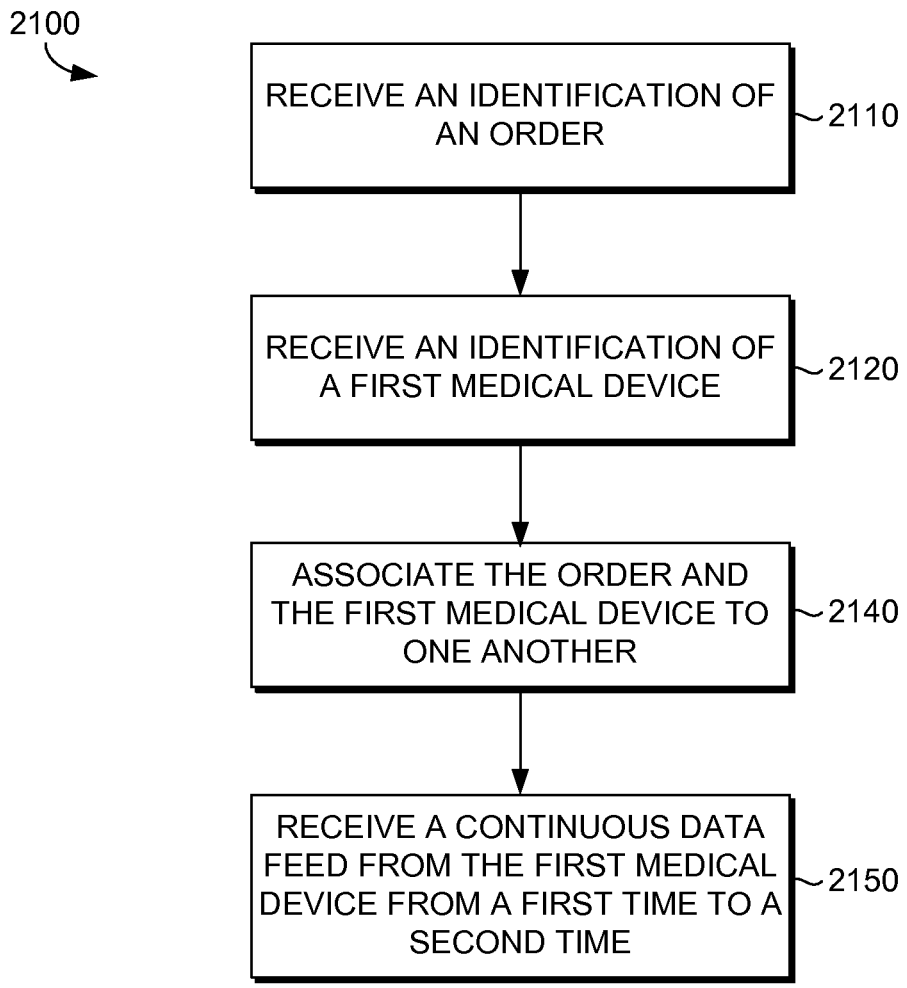
FIG. 21 is an illustrative flow diagram of a method for associating an order to one or more medical devices, in accordance with an embodiment of the present invention.

Turning to FIG. 21, an illustrative flow diagram 2100 is shown of a method for associating an order to one or more medical devices, in accordance with an embodiment of the present invention. Initially, an identification of an order is received at step 2110. The identification of the order may be received in accordance with one of the methods described above, or any other method that allows for its identification. At step 2120, an identification of a first medical device is received. According to some embodiments, an identification of a second medical device could also be received. Similar to the identification of the order, any method of identification described herein, or any other method that allows for the identification of a device, may be used. In response to receiving the identifications of the order and the first medical device, the order and the first medical device are then associated to one another at step 2140.

A continuous data feed from the first medical device is received at step 2150, and the data may continually be received from a first time to a second time. In one embodiment, the first time occurs upon the initial association of the order to the first medical device, and the second time occurs upon a termination of the association of the order to the first medical device, such as upon the occurrence of a disassociation event, as described above. Like associations between devices and patients, multiple orders may be associated to a device at the same time, or multiple devices may be associated to an order at the same time. Therefore, the second medical device may be associated to the identified order and may maintain that association until the occurrence of a disassociation event.

Figure 22:
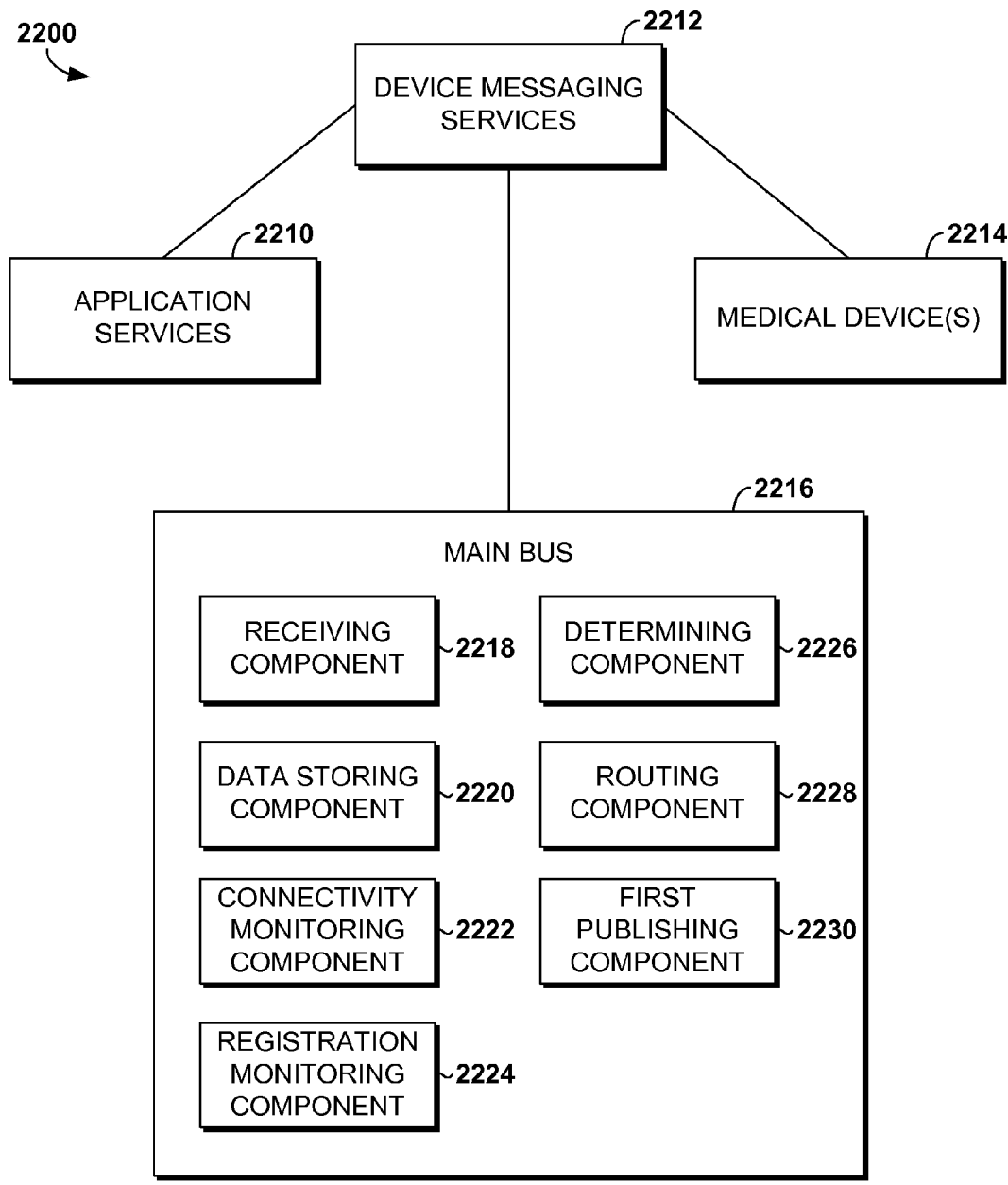
FIG. 22 is an block diagram of an exemplary system, according to an embodiment of the present invention.

FIG. 22 is a block diagram of an exemplary system, according to an embodiment of the present invention. Initially, application services 2210 may comprise several components, such as a database, various services that request and utilize data from medical devices (e.g., aggregation service, data store service, patient to device association services, chart documentation service), and various applications on which the services run. Application services 2210 is described in further detail herein in the discussion of FIG. 2. Device messaging services 2212 includes a main bus, which is a central bus or server that is responsible for receiving and delivering data from medical devices to various applications and services. Device messaging services is described in further detail herein in the discussion of FIG. 2. Medical devices 2214 includes any medical devices and associated components (e.g., device gateways, connectivity engine, device adapters) that are or may be connected, directly or indirectly, to the main bus, such as main bus 246 in FIG. 2.

The main bus 2216, as described above, includes a plurality of components, each being responsible for tasks associated with providing data from the medical devices to various services and applications. A receiving component 2218 may continually receive data from at least one medical device 214 during a period of time when the medical device(s) is online. A device is online when the main bus 2216 is able to receive data from it. The data may be received from a direct feed, and may be received directly from the medical device, a device gateway, or a connectivity engine. A connectivity engine may be used for legacy devices that do not have the required connection mechanisms. In some instances, legacy devices are older devices, and may not have the most up-to-date connection mechanisms. The connectivity engine may assist in allowing even many legacy devices to be connected to it, so that the device can work with newer components.

A data storing component 2220 stores the continually received data from the medical device(s) 2214 so that the data can be accessed for querying and archiving. For example, once the data is stored, a user, such as a clinician, may want to search for particular data associated with a certain patient and a medical device. For this reason, the data that is stored may later be archived such that is can be queried.

A connectivity monitoring component 2222 monitors whether the devices are connected to the main bus 2216. This is done so that the main bus 2216 knows whether it can receive data from a particular medical device. If a medical device is not connected, it may not be able to be associated with a patient, as data cannot be retrieved from it.

A registration monitoring component 2224 monitors the registration and deregistration of the medical devices, and may also maintain a registry of the registration and deregistration events. Once it is determined that a device is connected, such as by the connectivity monitoring component 2222, the device may need to be registered in order to communicate and sent data to and from the other components, such as the main bus 2216. When the device goes offline, it may deregister, and a list of these events may be maintained by the registration monitoring component 2224.

A determining component 2226 determines a patient who is associated to the medical device, so that the data from the medical device can be properly associated with that patient. Once associated, a routing component 2228 routes the data from the medical device(s) to an electronic medical record (EMR) that corresponds to the patient. Further, a first publishing component 2230 publishes patient data (e.g., test results) corresponding to the medical device(s) to the EMR that corresponds to the patient. Data (e.g., test results) may be stored in a temporary storage until the results are transmitted to the EMR that corresponds to the patient.

In one embodiment, a second publishing component may publish digital media from the medical device(s) to the patient's EMR. Digital media may include video, audio, or other media that may need to be referenced regarding a patient in the future. In still another embodiment, a third publishing component may publish infusion data and infusion events into the patient's EMR, if the patient was associated with an infusion device, such as an infusion pump. The infusion data may include a rate of infusion (i.e., infusion rate) and a volume infused. The infusion events may include an infusion rate change or a time when the infusion begins or ends.

Figure 23:
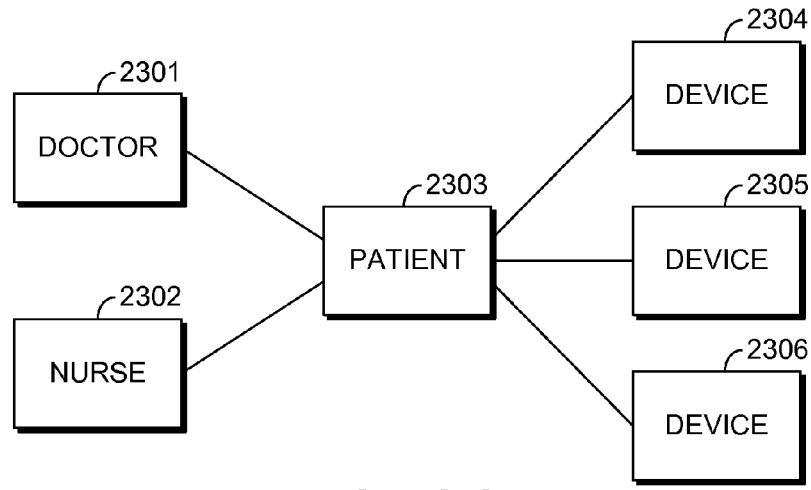
FIG. 23 is a block diagram of a network of clinicians, patients, and devices suitable for embodiments of the invention.

Turning now to FIG. 23, a block diagram depicting a group of clinicians 2301, 2302 and a patient 2303 is given. Clinicians 2301, 2302 could wish to be associated with the medical devices 2304, 2305, 2306 that are used to treat and monitor patient 2303. Clinicians can include a number of different jobs, for example a doctor 2301 and a nurse 2302 could make up a pair of clinicians 2301, 2302. There are other types of clinicians that could be supported by the invention. Each clinician 2301, 2302 could request association with patient 2303. According to some embodiments, such associations could be automatically requested upon admitting patient 2303. According to other embodiments, the associations could be requested by various staff members on behalf of the clinicians 2301, 2302. Upon identifying patient 2303, a list of medical devices 2304, 2305, 2306 could be retrieved as being associated with patient 2303. The medical devices 2304, 2305, 2306 in the list could then be associated with the clinicians 2301, 2302.

Figure 24:
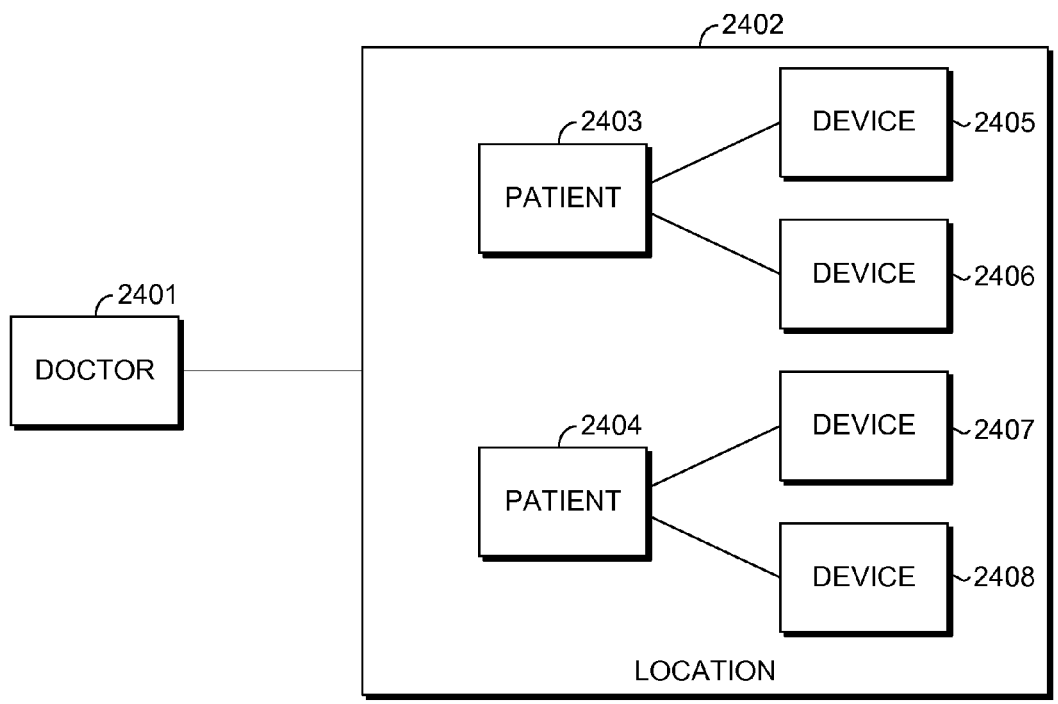
FIG. 24 is a block diagram of a network of clinicians, patients, and devices suitable for embodiments of the invention.

Turning now to FIG. 24, a block diagram depicting a doctor 2401 that would like to be associated with a group of patients 2403, 2404. There are a number of ways that patients 2403, 2304 could be grouped, in accordance with an embodiment of the invention. For example, groups of patients 2403, 2404 could be identified by a location 2402. A clinician 2401 could choose a location 2402 to be associated with. In this case, patients 2403, 2404 within the location 2402 could then be associated with the clinician 2401. Each medical device 2405, 2406, 2407, 2408 could be associated with the clinician 2401 due to their association with patients 2403, 2404, in the selected location 2402.

If a clinician 2401 chooses a location 2402 to be associated with, then a mechanism to automatically associate new patients entering the location and to disassociate patients leaving the location is used, in accordance with embodiments of the invention. By way of example, upon entering or leaving a particular location, electronic records could be used to track the location of the patients. Changes in these records could trigger associations or disassociation to any clinicians currently associated with the location.

Figure 25:
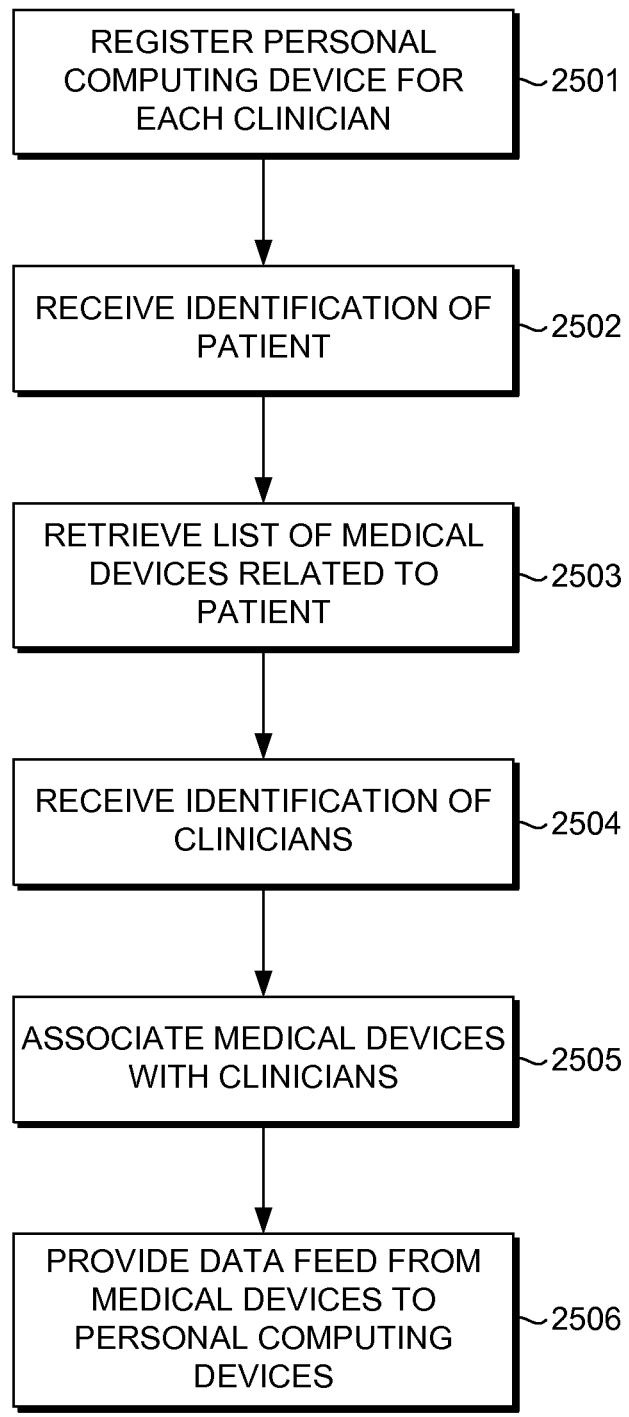
FIG. 25 is a flow diagram depicting a method of providing data feeds from medical devices to an associated clinician, in accordance with an embodiment of the invention.

Turning now to FIG. 25, a flow diagram depicting a method of providing data feeds to devices associated with one or more clinicians is given. Computing devices for each clinician are registered, as shown at block 2501. According to some embodiments, each clinician, upon starting a shift, could register their current computing device. According to other embodiments, clinicians could be assigned particular computing devices to be used. Such an assignment could be for various lengths of time. For example, monthly personal computing device assignments could be made.

An identification of a patient is made, as shown at block 2502. According to some embodiments, the identification of a patient could be made by the clinician. According to other embodiments, patients could be assigned to clinicians at various times. For example, upon being admitted, a patient could be assigned to one or more clinicians and identifications could be generated. A list of medical devices is retrieved, as shown at block 2503. The list of medical devices could include all devices used to treat and monitor the identified patient. According to some embodiments, the list of medical devices could include a subset of the medical devices used to treat and monitor the patient. For example, the list of medical devices could include only medical devices used to monitor the patient.

An identification of a clinician is received, as shown at block 2504. The identification of the clinician could be received from a number of sources. By way of example, if a clinician identifies the patient, as shown at block 2502, then the identification of the clinician could generated from the identification of the patient. As another example, the identification of the clinician could be generated by different staff member as the patient is admitted. There are many other ways in which a clinician could be identified, in accordance with the invention.

The medical devices from the list of medical devices are associated with the computing devices associated with the identified clinician, as shown at block 2505. Data feeds are provided to the computing devices from the medical devices, as shown at block 2506. The data feeds could be continuous feeds of data. For example, the data feeds could be continuous data feeds showing patient health information. As another example, the data feeds could include alerts. For example, an IV pump may indicate that an infusion is complete. Such an alert could be sent continuously once the infusion is complete. As another example, a bed monitor could send an alert that a patient is attempting to leave the bed.

According to some embodiments of the invention, when a patient is discharged, an indication of the patient leaving could be generated. The indication could cause a list of medical devices associated with the leaving patient to be generated. The medical devices in the list could then be disassociated from the computing device of any clinicians associated with the leaving patient.

According to a further embodiment, new medical devices could be associated with a patient that is associated with some clinicians. An indication that the new medical devices have been associated with the patient could be generated. The new medical device could be associated with each of the computing devices for each of the clinician to which the patient is associated.

Data feeds could be divided into a number of tiers. Tiers could be used to separate data according to a number of different characteristics. For example, one tier could contain monitoring devices and another tier could include medical devices used to treat patients. Various tiers could be associated with various clinicians.

Figure 26:
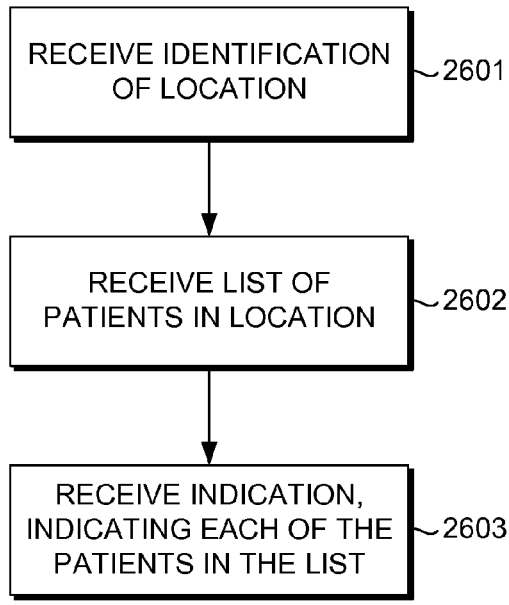
FIG. 26 is a flow diagram depicting a method of identifying patients to associate with a clinician, in accordance with an embodiment of the invention.

Turning now to FIG. 26, a method of identifying patients in a particular location is given. An identification of a location is received, as shown at block 2601. An identification of a location could come from a particular clinician. For example a clinician could indicate they wish to associate themselves to any patient on a particular unit. An identification of a location could also be given by a staff member on behalf of a clinician. For example, identifications of locations could be made when schedules for clinicians are made.

A list of patients within the location is retrieved, as shown at block 2602. The list could be retrieved from patient admittance records, according to an embodiment of the invention. Identifications for each patient in the list could be generated, as shown at block 2603. According to some embodiments of the invention, the indication of location for a clinician could be automatically generated according to some pre-defined period of time. New lists of patients could be generated each time, depending on patients being admitted or discharged. As another example, a new patient being admitted could be used to trigger a new list creation, thereby generating the identification of the new patient.

Figure 27:
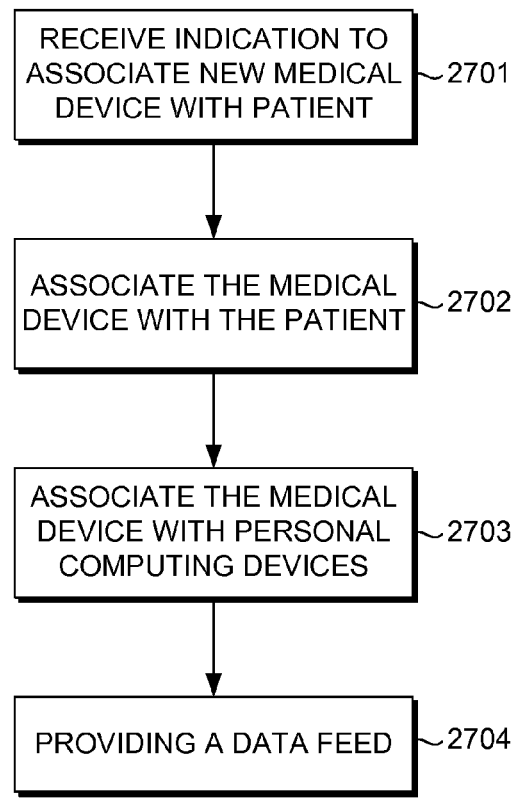
FIG. 27 is a flow diagram depicting a method of providing a data feed from medical devices to an associated clinician, in accordance with an embodiment of the invention.

Turning now to FIG. 27, a flow diagram depicting a method of providing a data feed from a newly associated patient medical device is given. An indication to associate a new medical device with a patient is received, as shown at block 2701. The new medical device is associated with the patient, as shown at block 2702. There are a number of ways, according to embodiments of the invention to associate new medical devices with a patient. The new medical device is associated with the computing devices of each clinician that is associated with the patient, as shown at block 2703. For example, a list of clinicians currently associated with the patient could be generated. This list could include a list of each clinicians computing devices. The new medical device could then be associated with the computing devices in the lists. A data feed from the new medical device is provide to each of the associated computing devices, as shown at block 2704. The data feeds could be similar to the data feeds in block 2506 of FIG. 25.

Figure 28:
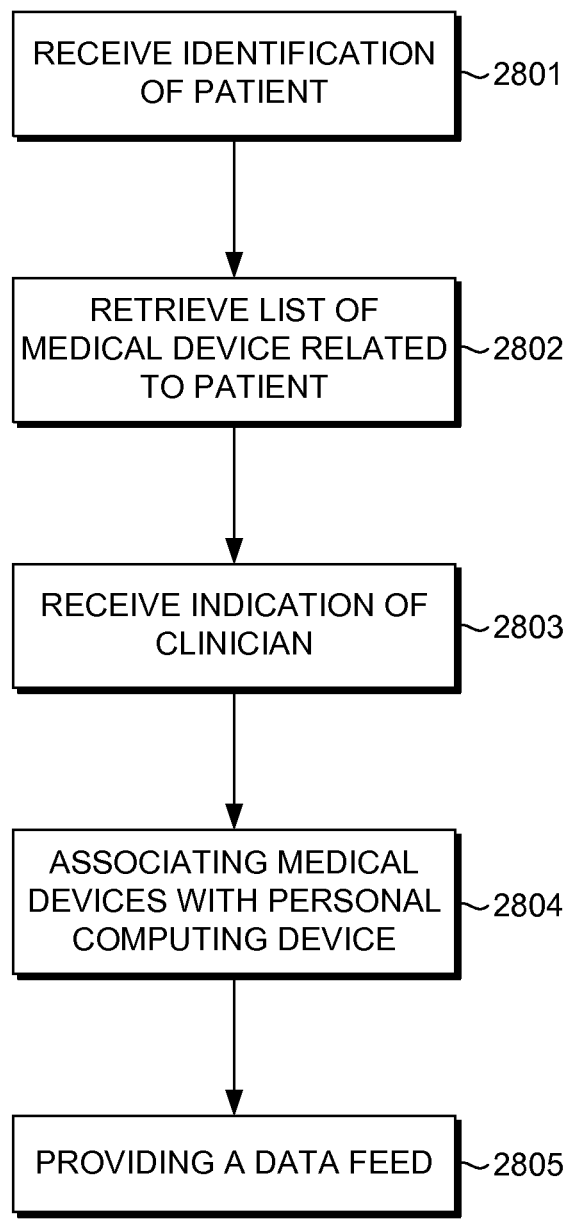
FIG. 28 is a flow diagram depicting a method of providing data feeds from medical devices to an associated clinician, in accordance with an embodiment of the invention.

Turning now to FIG. 28, a flow diagram depicting a method of providing a data feeds from medical devices associated with a patient to the computing devices associated with clinicians. A patient identification is received, as shown at block 2801, similar to block 2502 of FIG. 25 and a list of medical devices related to the patient is retrieved, as shown at block 2802, similar to block 2503 of FIG. 25. An identification of a clinician is received, as shown at block 2803, similar to block 2504 of FIG. 25. The medical devices in the list of medical devices are associated with the computing devices associated with the clinician, as shown at block 2804, similar to block 2505 of FIG. 25 and providing data feeds from the medical devices to the associated computing devices, as shown at block 2805, similar to block 2506 of FIG. 25.

Figure 29:
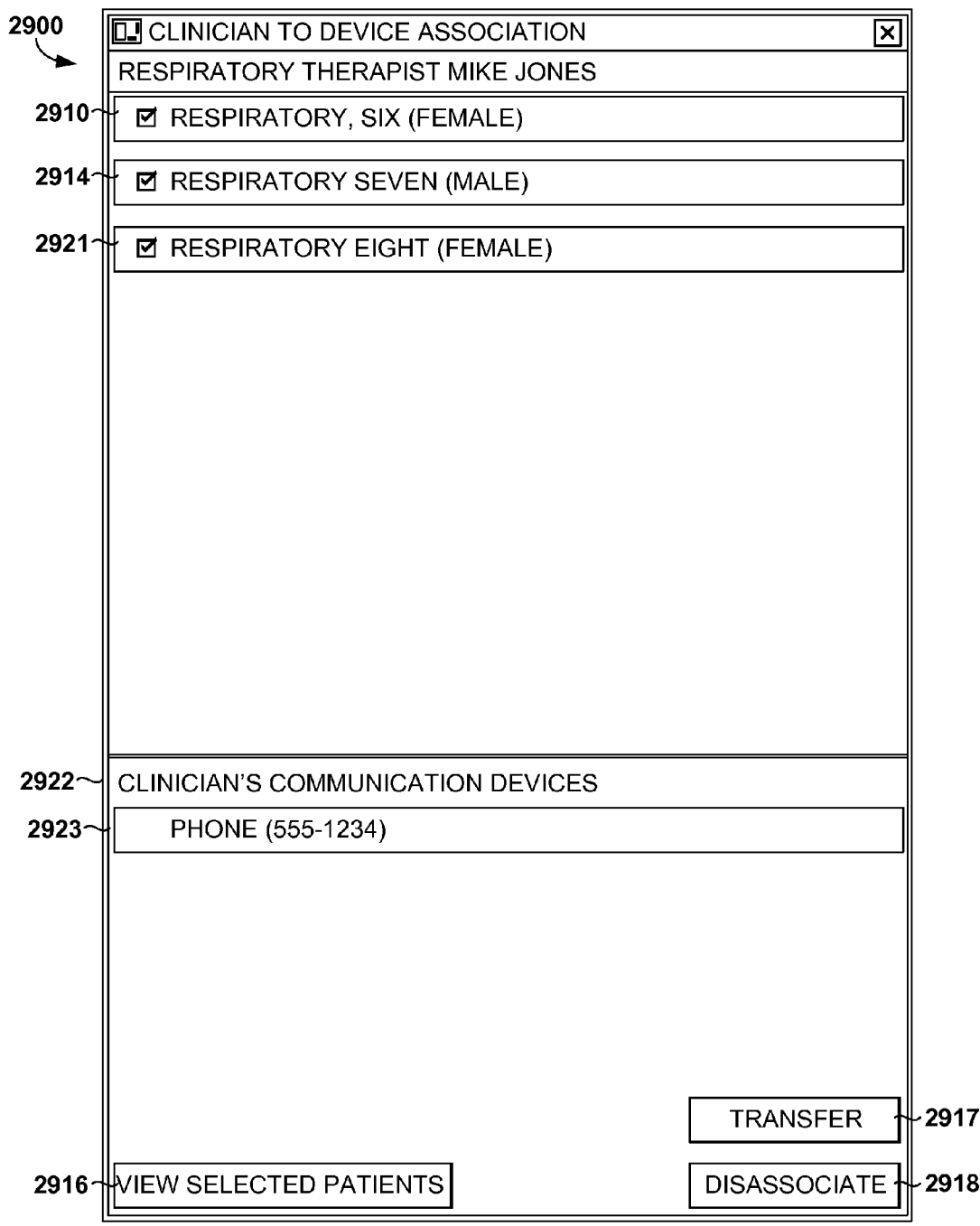
FIG. 29 is an illustrative screen display depicting a particular clinician.

With continued reference to FIG. 29, a clinician has been identified, as shown as clinician identification area 2900. A list of patients associated with the clinician is displayed 2910, 2914, 2921. Each patient identification box 2910, 2914, 2921 could contain various types of patient identification information, including, but not limited to, the patient's name, gender, date of birth, identification number, and the like. A patient may be identified by a variety of means. For instance, a patient may be identified by scanning a barcode that is located on or near the patient. When a patient is admitted to a hospital, for example, the patient may wear a wristband that has a barcode such that the patient may be easily identified. Alternatively, a patient's bed may have the patient's identification located somewhere on it for quick access. Another form of identification may be used instead of a barcode, such as a patient identification number or other identification form that may be entered into a mobile computing device (e.g., PDA) to identify the patient.

Clinician communication device display area 2922 may display any communication devices associated with the clinician. For example, a phone 2923 could be listed as an associated communication device. Many associated communication devices could be listed as being associated with the clinician. By way of example, such devices could include laptops, computer terminals at the hospital, personal digital assistants, and netbooks. Various information related to the associated communications devices could be listed along with the device name 2923. For example, such information could include, a phone number, an Internet Protocol address, a fully qualified domain name, and the like.

Interface buttons at the bottom of the display screen 2916, 2917, 2918, can be used to interact with the list of patients 2910, 2914, 2921. A patient can be selected and the "View Selected Patients" button can be used to view information and devices related to the selected patients (See FIG. 30). The "Transfer" button 2917 could be used to transfer a patient to another clinician (See FIG. 31). The "Disassociate" button 2918 could be used to remove a patient from the list of patients 2910, 2914, 2921.

Figure 30:
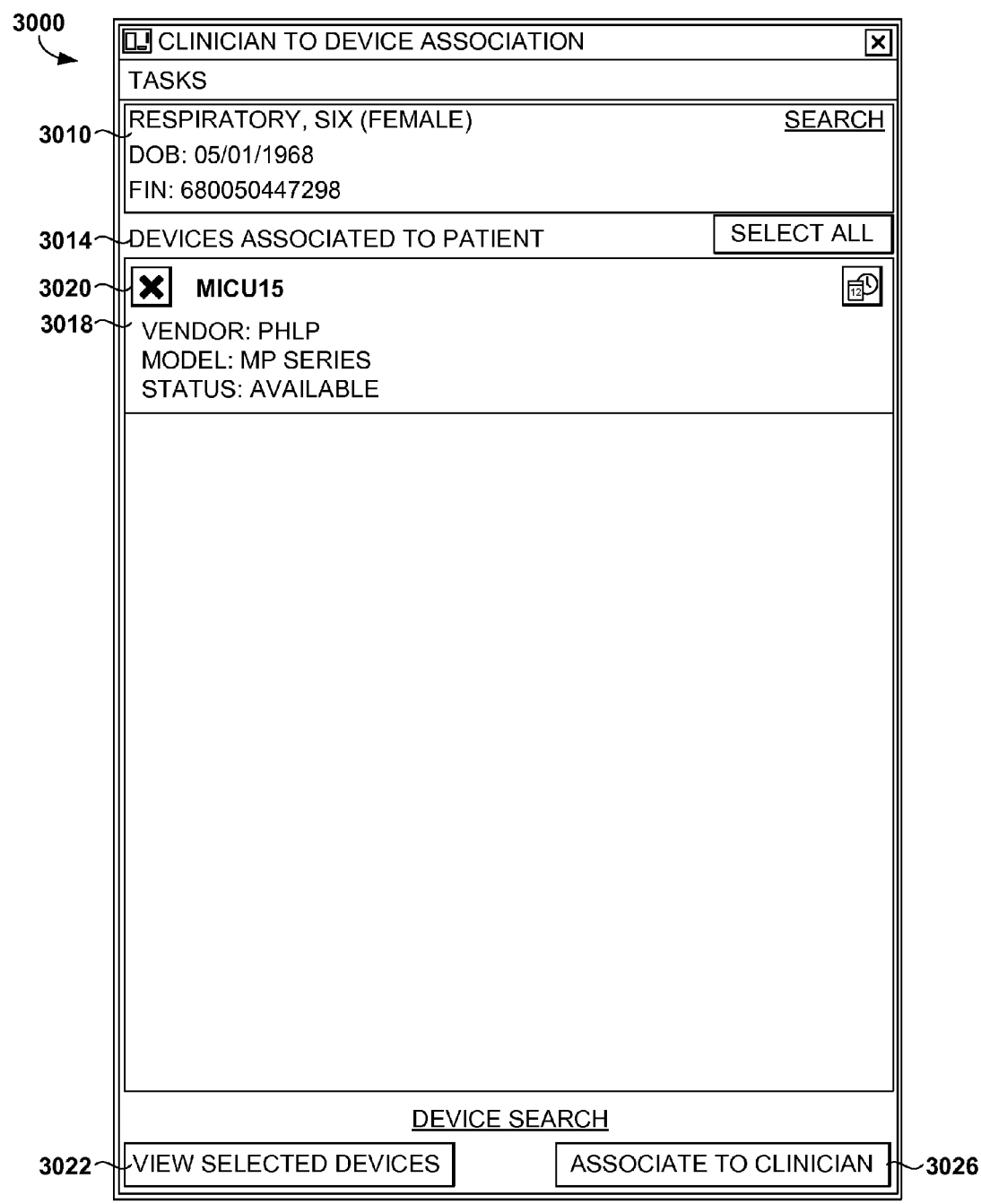
FIG. 30 is an illustrative screen display depicting a patient and some associated devices.

Turning now to FIG. 30, a display screen depicting a patient with a list of associated devices is given 3000. A particular patient is listed 3010 along with various information about the patient. For example, such information can include the patient's name, gender, date of birth, identification number, and the like. In the associated device section of the screen 3014, various devices are listed (e.g., 3018). Information about each device can be listed in the device information section 3018. Such information could include device name, vendor, model information, and status. A checkbox 3020 can be used to allow the selection of particular devices. Once a device is selected, the "View Selected Devices" button can be used to display a list of clinicians who are associated with the selected devices. Additionally, if a clinician wishes to become associated with a particular device, the "Associate" button 3026 will associated the clinician with the selected device or devices.

Figure 31:
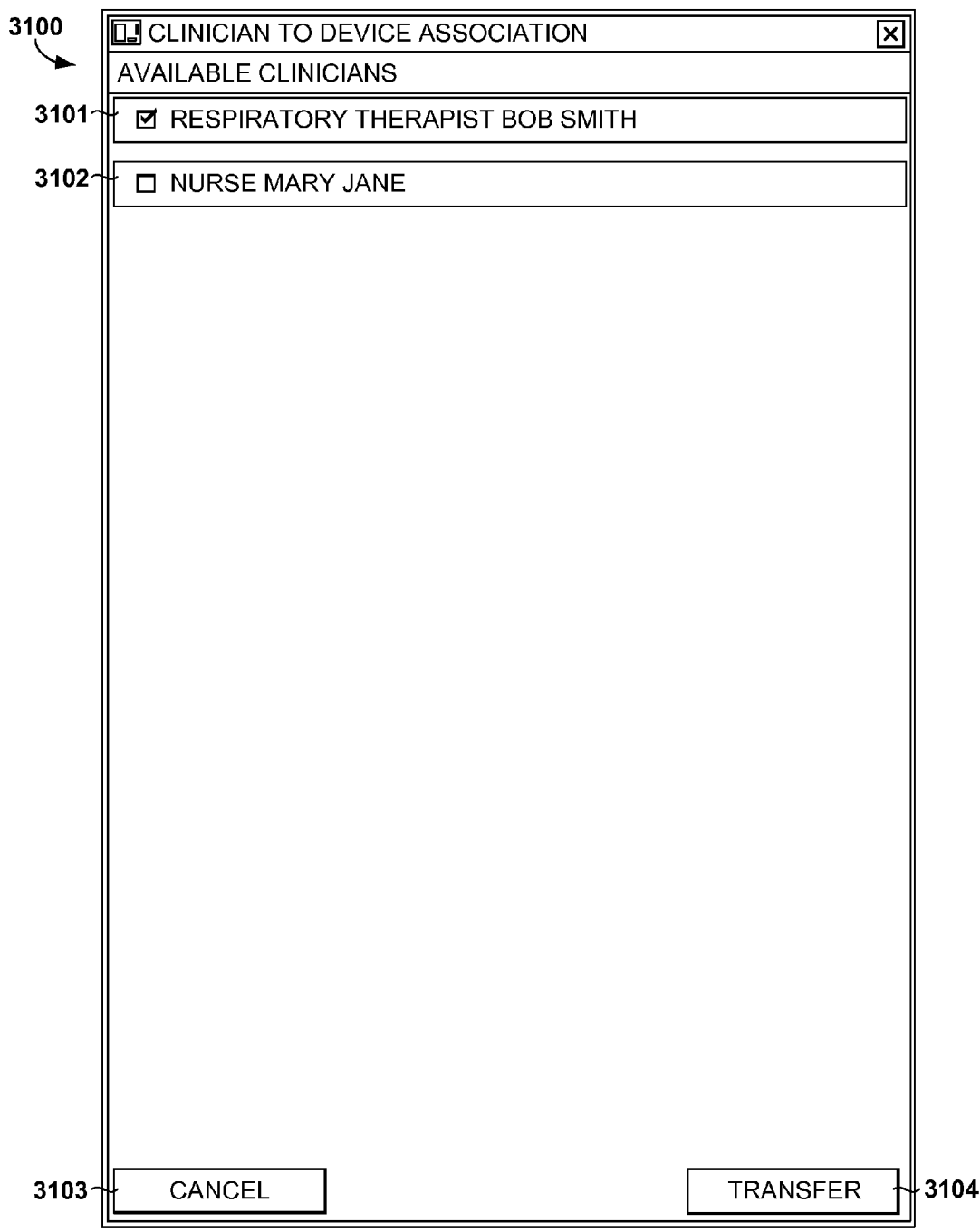
FIG. 31 is an illustrative screen display depicting a number of clinicians.

Turning now to FIG. 31, a display screen 3100 that can be used to transfer an associated patient device to another clinician is displayed. A list of available clinicians is displayed 3101, 3102. Each clinician box 3101, 3102 contains a checkbox used for selecting the clinician and various information about each clinician. By way of example, such information can include name, department, specialty, phone number, and the like. Once one or more clinicians are selected, the "Transfer" button 3104 can be used to transfer the patients and devices selected using the display screen discussed with reference to FIG. 29 to the selected clinicians. The display screen 3100 also provides a "Cancel" button 3103 for use in returning to the display screen depicted in FIG. 29 without transferring any patient devices.

It will be understood that certain features and sub-combinations of utility may be employed without reference to features and sub-combinations and are contemplated within the scope of the claims. Furthermore, the steps performed need not be performed in the order described.

The invention claimed is:

1. Non-transitory computer-readable media having computer-executable instructions embodied thereon that, when executed, enable a computing device to perform a method of providing one or more clinicians a plurality of data feeds from a plurality of devices related to a patient, the method comprising:
    registering one or more computing devices and associating the one or more computing devices with a first clinician;
    receiving an identification of a patient;
    associating the patient with the first clinician;
    determining, by a connectivity monitoring component, one or more medical devices connected to a main bus, and generating a list of one or more connected medical devices related to the patient;
    receiving a selection of at least one connected medical device of the list of one or more connected medical devices;
    based on the selection, registering the at least one selected medical device with the main bus, wherein registering the at least one selected medical device enables communication between the at least one selected medical device and the main bus;
    associating the at least one selected medical device with the one or more computing devices associated with the first clinician;
    providing, by a routing component, a data feed from each of the at least one selected medical device such that the data feed is selectively routed to the one or more computing devices associated with the first clinician; and
    maintaining the data feed until a direct transfer of the at least one selected medical device from the first clinician to a transfer clinician is received.

2. The media of claim 1, wherein the one or more computing devices comprise a mobile phone.

3. The media of claim 1, wherein the identification of the patient is received from the first clinician.

4. The media of claim 1, wherein receiving an identification of the patient includes:
    receiving an identification of a location;
    receiving a list of one or more patients in said location; and
    receiving an indication, indicating each of the one or more patients in the list.

5. The media of claim 4, further comprising:
    receiving an indication that a first patient from the list of patients is leaving, identifying the first patient as a leaving patient; and
    disassociating one or more connected medical devices from each computing device of the one or more computing devices of the first clinician, wherein the one or more connected medical devices being disassociated are also associated with the leaving patient.

6. The media of claim 1, further comprising:
    receiving an indication to associate a new connected medical device with the patient;
    associating the new connected medical device with the patient;
    associating the new connected medical device with each computing device of the one or more computing device of the first clinician; and
    providing a data feed from the new connected medical device to each computing device of the one or more computing devices of the first clinician.

7. The media of claim 1, further comprising receiving an identification of one or more additional clinicians and associating the one or more additional clinicians with the one or more connected medical devices.

8. The media of claim 1, wherein the data feed is a continuous data feed of information from the at least one selected medical device.

9. The media of claim 1, wherein the data feed includes a continuous feed of alerts from at least one selected medical device.

10. The media of claim 8, wherein the continuous data feed of information is divided into tiers.

11. The media of claim 10, wherein each tier is accessible to a subset of clinicians.

12. The media of claim 11, wherein clinicians include doctors and nurses.

13. Non-transitory computer-readable media having computer-executable instructions embodied thereon that, when executed, enable a computing device to perform a method of providing one or more clinicians a plurality of data feeds from a plurality of devices related to a patient, the method comprising:

receiving an identification of a patient;

determining, by a connectivity monitoring component, one or more medical devices connected to a main bus, and generating a list of one or more connected medical devices related to the patient;

receiving a selection of at least one connected medical device of the list of one or more connected medical devices;

based on the selection, registering the at least one selected medical device with the main bus, wherein registering the at least one selected medical device enables communication between the at least one selected medical device and the main bus;

receiving an indication of a clinician and an associated computing device;

associating the at least one selected medical device related to the patient with the clinician;

providing a data feed from the at least one selected medical device related to the patient such that the data feed is selectively routed to the associated computing device of the clinician;

maintaining the data feed until a direct transfer of the at least one selected medical device from the clinician to a transfer clinician is entered; and providing, on the associated computing device of the clinician, an interface for:

deselecting the clinician associated with the at least one selected medical device related to the patient;

selecting the transfer clinician associated with an associated transfer clinician computing device; and associating the transfer clinician with the at least one selected medical device related to the patient.

14. The media of claim 13, wherein the identification of the patient is received from the clinician.

15. The media of claim 13, wherein receiving the identification of the patient includes:

receiving an identification of a location;

receiving a list of one or more patients in said location; and receiving an indication, indicating each of the one or more patients in said location.

16. The media of claim 15, further comprising:

receiving an indication that a first patient from the list of patients is leaving, identifying the first patient as a leaving patient; and disassociating one or more connected medical devices from the computing device, wherein the one or more connected medical devices being disassociated are also associated with the leaving patient.

17. The media of claim 13, further comprising:

receiving an indication to associate a new connected medical device with the patient;

associating the new connected medical device with the patient;

associating the new connected medical device with the computing device; and providing a data feed from the new connected medical device to the computing device.

18. The media of claim 13, wherein the data feed is a continuous data feed of information from the at least one selected medical device.

19. The media of claim 13, wherein the data feed includes a continuous feed of alerts from the at least one selected medical device.

20. Non-transitory computer-readable media having computer-executable instructions embodied thereon that, when executed, enable a computing device to perform a method of providing one or more clinicians a plurality of data feeds from a plurality of devices related to a patient, the method comprising:

registering a computing device for one or more clinicians as an associated computing device;

receiving an identification of a patient from one or more clinicians;

determining, by a connectivity monitoring component, one or more active medical devices connected to a main bus, and generating a list of one or more active connected medical devices related to the patient;

receiving a selection of one or more connected medical devices of the list of one or more active connected medical devices;

based on the selection, registering the one or more selected medical devices with the main bus, wherein registering the one or more selected medical devices enables communication between the one or more selected medical devices and the main bus;

receiving an identification of one or more clinicians as identified clinicians;

associating the one or more selected medical devices related to the patient with the associated computing device;

providing a data feed from each of the one or more selected medical devices related to the patient such that the data feed is selectively routed to the associated computing device of the one or more identified clinicians; and maintaining the data feed until the one or more selected medical devices are disassociated; and providing, on the associated computing device of the one or more identified clinicians, an interface for:

selecting the one or more identified clinicians associated with the computing device;

selecting the one or more patients having one or more selected medical devices; and disassociating the one or more identified clinicians from the one or more patients.

* * * * *